(12) United States Patent
Darveau et al.

(10) Patent No.: US 7,622,128 B2
(45) Date of Patent: Nov. 24, 2009

(54) PORPHYROMONAS GINGIVALIS 1435/1449 LPS AS AN IMMUNE MODULATOR

(75) Inventors: Richard P. Darveau, Redmond, WA (US); Robert Reife, Redmond, WA (US); Keith Knutson, Rochester, MN (US)

(73) Assignee: University of Washington, Seattle, WA (US)

( * ) Notice: Subject to any disclaimer, the term of this patent is extended or adjusted under 35 U.S.C. 154(b) by 198 days.

(21) Appl. No.: 11/301,542

(22) Filed: Dec. 13, 2005

(65) Prior Publication Data

US 2007/0134170 A1 Jun. 14, 2007

(51) Int. Cl.
A61K 45/00 (2006.01)
A61K 47/00 (2006.01)
A61K 49/00 (2006.01)

(52) U.S. Cl. .................. 424/278.1; 424/9.1; 424/9.2; 424/184.1; 424/234.1; 424/282.1; 435/4; 435/7.1; 435/7.2

(58) Field of Classification Search .............. 424/9.1, 424/9.2, 184.1, 234.1, 278.1, 282.1; 435/4, 435/7.1, 7.2

See application file for complete search history.

(56) References Cited

U.S. PATENT DOCUMENTS

| | | | |
|---|---|---|---|
| 4,436,727 A | 3/1984 | Ribi | |
| 4,866,034 A | 9/1989 | Ribi | |
| 4,877,611 A | 10/1989 | Cantrell | |
| 4,912,094 A | 3/1990 | Myers et al. | |
| 4,987,237 A | 1/1991 | Myers et al. | |
| 5,508,310 A | 4/1996 | Rhodes | |
| 5,654,289 A | 8/1997 | Kodama et al. | |
| 6,218,166 B1 | 4/2001 | Ravindranath et al. | |
| 6,491,919 B2 | 12/2002 | Crane | |
| 6,800,613 B2 | 10/2004 | Persing et al. | |
| 6,818,221 B2 * | 11/2004 | Pulendran et al. | ........ 424/234.1 |
| 6,911,434 B2 | 6/2005 | Baldridge et al. | |
| 2005/0002945 A1 | 1/2005 | McBride et al. | |
| 2005/0136065 A1 | 6/2005 | Valiante | |

OTHER PUBLICATIONS

Darveau, R.P., et al. Infection and Immunity, vol. 72, No. 9, pp. 5041-5051, 2004.*

Bainbridge and Darveau, "*Porphyromonas gingivalis* Lipopolysaccharide: an Unusual Pattern Recognition Receptor Ligand for the Innate Host Defense System," *Acta. Odontol. Scand.* 59:131-138 (2001).

Cohen et al., "Induction of Tolerance by *Porphyromonas gingivalis* on APCs:a Mechanism Implicated in Periodontal Infection," *J. Dent. Res.* 83:429-433 (2004).

Darveau et al., "Ability of Bacteria Associated With Chronic Inflammatory Disease to Stimulate E-Selectin Expression and Promote Neutrophil Adhesion," *Infect. Immun.* 63:1311-1317 (1995).

Hashimoto et al., "Separation and Structural Analysis of Lipoprotein in a Lipopolysaccharide Preparation from *Porphyromonas gingivalis*," *Int. Immunol.* 16:1431-1437 (2004).

Kumada et al., "Structural Study on the Free Lipid A Isolated From Lipopolysaccharide of *Porphyromonas gingivalis*," *J. Bacteriol.* 177:2098-2106 (1995).

Ogawa, "Chemical Structure of Lipid A from *Porphyromonas (Bacteroides) gingivalis* Lipopolysaccharide," *FEBS Lett.* 332:197-201 (1993).

Ogawa, "Immunopharmacological Activities of the Nontoxic Monophosphoryl Lipid A of *Porphyromonas gingivalis*," *Vaccine* 14:70-76 (1996).

Poltorak et al., "Physical Contact Between Lipopolysaccharide and Toll-like Receptor 4 Revealed by Genetic Complementation," *Proc. Natl. Acad. Sci. USA* 97:2163-2167 (2000).

Somerville et al., "A Novel *Escherichia coli* Lipid A Mutant That Produces an Antiinflammatory Lipopolysaccharide," *J. Clin. Invest.* 97:359-365 (1996).

Yi and Hackett, "Rapid Isolation Method for Lipopolysaccharide and Lipid A from Gram-Negative Bacteria," *Analyst* 125:651-656 (2000).

Kugler et al., "Regression of human metastatic renal cell carcinoma after vaccination with tumor cell-dendritic cell hybrids," *Nature Medicine* 6:332-336 (2000).

* cited by examiner

*Primary Examiner*—Rodney P. Swartz
(74) *Attorney, Agent, or Firm*—Townsend and Townsend and Crew LLP

(57) ABSTRACT

A preparation containing lipopolysaccharide (LPS) of *Porphyromonas gingivalis* having a molecular negative mass ion of 1435 or 1449 is used as an immune system modulator to redirect a host's immune system against an antigen of interest. The 1435/1449 LPS preparation can be isolated from *P. gingivalis* or prepared as a derivative or mimetic thereof. The immunomodulating preparations of *P. gingivalis* 1435/1449 can be used as a vaccine adjuvant, and can be used to stimulate an immune response against a selected antigen associated with a disease of interest, such an antigen associated with a tumor, infectious disease, autoimmune disease, MHC antigen, or to modulate asthma or other inflammatory conditions.

23 Claims, 16 Drawing Sheets

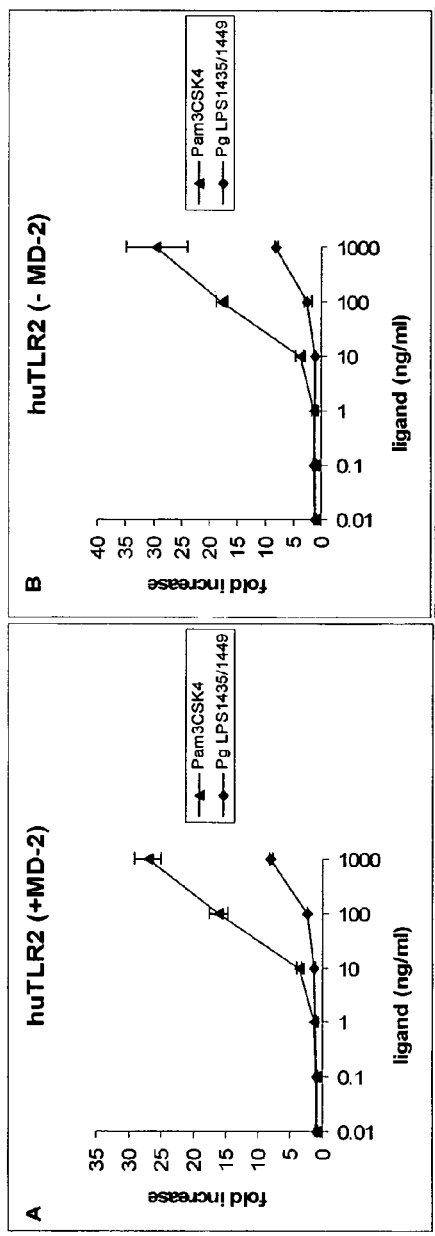
Fig. 7A / Fig. 7B
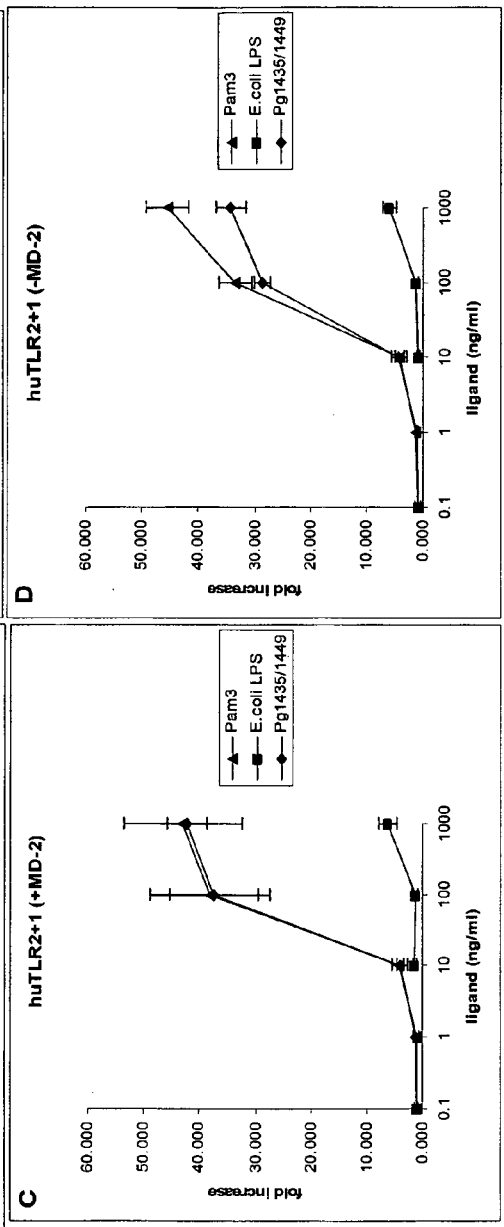
Fig. 7C / Fig. 7D

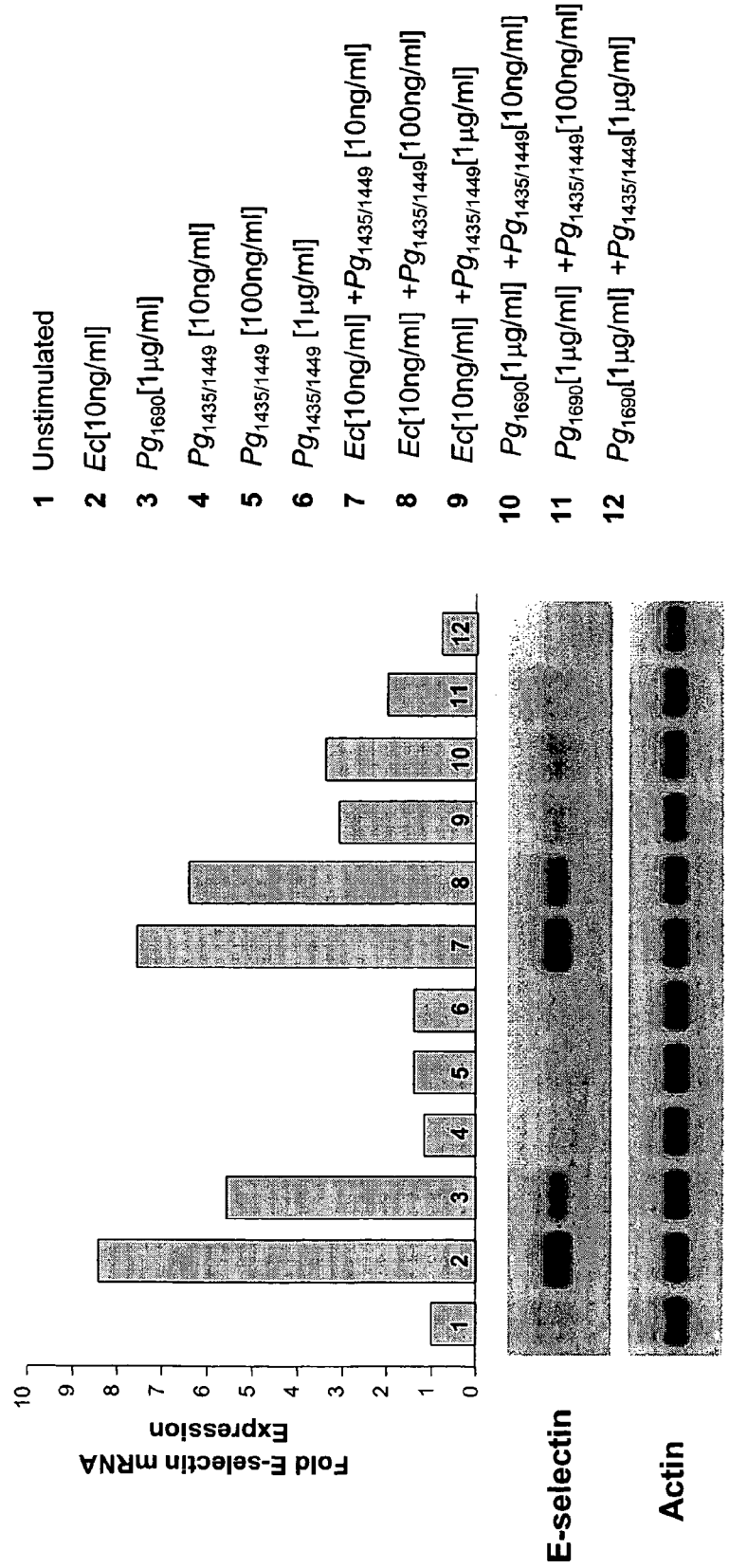

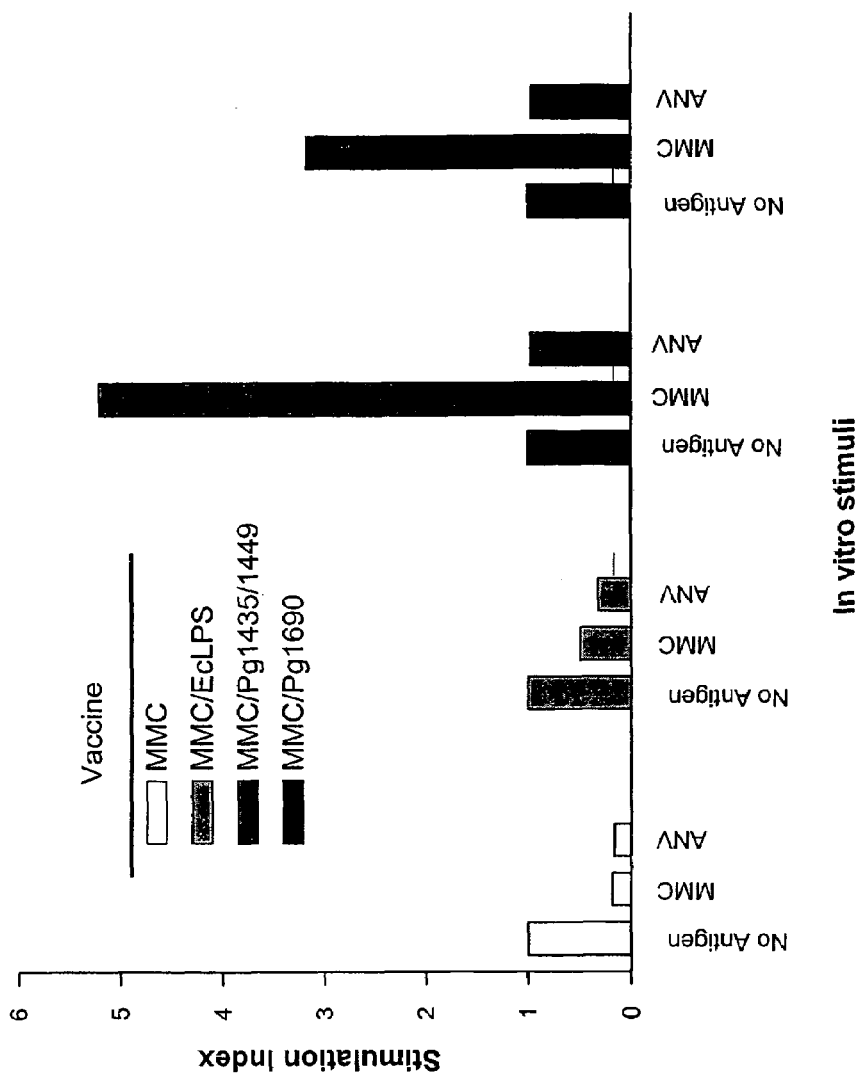

US 7,622,128 B2

PORPHYROMONAS GINGIVALIS 1435/1449 LPS AS AN IMMUNE MODULATOR

STATEMENT AS TO RIGHTS TO INVENTIONS MADE UNDER FEDERALLY SPONSORED RESEARCH OR DEVELOPMENT

The present invention was developed in part with government support under grant numbers R01 DE12768, T32 DE07023, and R01 CA85374 awarded by the National Institutes of Health. The government may have certain rights in this invention.

BACKGROUND OF THE INVENTION

A functional host immune system consists of different host components (e.g. effector cells and molecules) that act coordinately to recognize microbial infections, dying, and malignant tissue and elicit the appropriate responses, respectively. The immune system is divided into 2 broad categories, the innate and adaptive immune responses. The innate immune response consists of a variety of cellular and molecular effectors such as dendritic cells, macrophages, eosinophils, neutrophils, and natural killer cells. The adaptive immune response consists of T lymphocytes, B lymphocytes, and natural killer T (NKT) cells. The innate and adaptive are intimately linked and often work jointly to maintain the overall health of the individual. T lymphocytes (T cells) refers to a family of both effector and regulatory cells. The helper (CD4 Th) T cells and the cytotoxic (CD8, CTL) T cells are the major effector T cells. CD4 Th cells support the development of an adaptive immune response by producing cytokines for B cells and CD8 T cells. CD4 T cells can be further subdivided into Th1, Th2, and Th17 cells, each with a specialized function in the immune response.

Adaptive and innate immune responses are regulated by regulatory T cells and NKT cells. The adaptive immune response is activated by the innate immune system and particularly macrophages and dendritic cells which have taken up antigen derived from dysfunctional or infected tissues. An inflammatory response refers to an active immune response that is mediated by one or more immune effectors of the innate and/or adaptive immune system.

Lipopolysaccharide (LPS), often called endotoxin as it is isolated from *E. coli* and other gram-negative bacteria, is a well known and potent inflammatory immune activator. Ulevitch and Tobias, *Curr. Opin. Immunol.* 11: 19-22 (1999). Several studies have validated the important role of LPS in triggering inflammation in response to bacterial infection. Although the chemical structure of LPS has been known for some time, the molecular basis of recognition of LPS by serum proteins and/or cells is only now being elucidated.

A family of receptors, referred to as Toll-like receptors, (TLRs), have been linked to LPS and other microbial components to activation of the adaptive and innate immune responses. TLRs are membrane proteins having a single transmembrane domain, a cytoplasmic domain that shares similarity with the cytoplasmic domain of the IL-1 receptor, and a relatively large extracellular domain that may contain multiple ligand-binding sites. The importance of TLRs in the immune response to LPS has been demonstrated for at least two TLRs, TLR2 and TLR4.

In addition to TLRs, at least two other proteins are part of the host innate defense pathway that responds to bacterial LPS. The lipopolysaccharide binding protein (LBP) is an acute-phase serum protein that binds LPS molecules. The LBP then facilitates the transfer of LPS to CD14, in its membrane-bound form as mCD14, and/or its soluble form found in serum, sCD14. The importance of CD14 in inflammation has been validated in mice, where CD14 was shown to be required for the development of sepsis.

One role of CD14 is to concentrate microbial components such as LPS on the host cell surface for further recognition by TLRs and the innate host response system. CD14 acts with TLRs as a co-receptor to facilitate activation of host cells. Transfer of *E. coli* LPS by either mCD14 or sCD14 to a cell-associated TLR4 and MD-2 protein complex has been shown to initiate host cell activation pathways leading to innate host defense mediator production. Muta and Takeshige, *Eur. J. Biochem.* 268:4580-4589 (2001); da Silva Correia et al., *J. Biol. Chem.* 276: 21129-21135 (2001).

The biologically active endotoxic moiety of LPS is lipid A, a phosphorylated, fatty acid-acylated glucosamine disaccharide that serves to anchor the entire LPS structure in the outer membrane of Gram-negative bacteria. Host responses to LPS vary significantly depending upon lipid A structure. Biological activity can be affected by the number, chain length, and position of lipid A fatty acids as well as the number of phosphate groups attached to the glucosamine disaccharide backbone. Takada and Kotani, 1992, Bacterial Endotoxic Lipopolysaccharides, Boca Raton: CRC Press; Loppnow et al., *J. Immunol.* 142: 3229-3238 (1989); and Schumann et al., *Blood* 87: 2805-2814 (1996).

Many efforts have been made to obtain nontoxic lipid A while retaining the beneficial activities. The toxic effects of lipid A can be ameliorated by selective chemical modification of lipid A to produce monophosphoryl lipid A compounds. Methods of making and using these compounds as immunostimulants, vaccine adjuvants, and as monotherapies, have been described. See, e.g., U.S. Pat. Nos. 4,436,727; 4,877,611; 4,866,034; 4,912,094; 4,987,237; 6,491,919; 6,800,613; and 6,911,434.

*Porphyromonas gingivalis* is a Gram-negative bacterium that is an important etiologic agent of adult type periodontitis. It releases large amounts of vesicles containing LPS that penetrate periodontal tissue and participate in a destructive innate host response associated with the disease. LPS and its lipid A component from *P. gingivalis*, however, do not elicit host responses in a manner similar to the classic *E. coli* endotoxin. *P. gingivalis* LPS is both less potent and it elicits a different pattern of inflammatory mediators when compared to *E. coli* LPS. For example, *P. gingivalis* LPS is not as potent an activator of human monocytes as *E. coli* LPS. Further, some *P. gingivalis* LPS fractions, unlike *E. coli* LPS, do not cause E-selectin expression on human endothelial cells, and some *P. gingivalis* LPS fractions are a natural antagonist of human endothelial cells and the IL-8 response to *E. coli* and other oral bacteria. Bainbridge, B. W. and Darveau, R. P., 1997, in Morrison, D., ed., Endotoxin in Health and Disease, New York, Marcel Dekker, p. 899-913. Based at least in part on differences in biological activities between *E. coli* and *P. gingivalis* LPS, the use of preparations of *P. gingivalis* LPS and lipid A and derivatives thereof to elicit a Th2 immune response has been proposed in U.S. Pat. No. 6,818,221 of Pulendran et al.

One structural study of the lipid A found in *P. gingivalis* LPS preparations showed that the major lipid A species is a tri-acylated monophosphorylated form with a negative ion mass of 1195. Ogawa, *FEBS Lett.* 332:197-201 (1993); see also, U.S. Pat. No. 5,654,289 to Kodama et al. In another study, multiple *P. gingivalis* lipid A structural isoforms were observed, however two forms predominated which were tetra-acylated monophosphorylated forms with molecular mass ions of 1435 and 1449, respectively. Kumada et al., *J.*

*Bacteriol.* 177:2098-2106 (1995). These structures and other isoforms found at m/z 1770 and 1690 are depicted in FIG. 1, and differ from the canonical *E. coli* lipid A structure in the number of phosphates, and the number, type, and position of the fatty acid chains. Another study employing tri-reagent to extract LPS has found that *P. gingivalis* contains multiple lipid A species. Yi and Hackett, *Analyst* 125:651-656 (2000).

Immune adjuvants are compounds which, when administered to an individual or tested in vitro, increase the immune response to an antigen in a subject to which the antigen is administered, or enhance certain activities of cells from the immune system. An adjuvant admixed or administered with, or during the course of antigenic stimulation is typically referred to as a vaccine or vaccination. The adjuvant provides the immune alerting or "danger" signal. A number of compounds exhibiting varying degrees of adjuvant activity have been prepared and tested. However, these and other prior adjuvant systems often display toxic properties, are unstable and/or have unacceptably low immunostimulatory effects.

An adjuvant presently licensed for human use in the United States is alum, a group of aluminum salts (e.g., aluminum hydroxide, aluminum phosphate) in which vaccine antigens are formulated. Particulate carriers like alum reportedly promote the uptake, processing and presentation of soluble antigens by macrophages. Alum, however, is not without side-effects and is unfortunately limited to humoral (antibody) immunity only.

The discovery and development of effective adjuvant systems is essential for improving the efficacy and safety of existing and future vaccines and other immunotherapies. Thus, there is a continual need for new and improved adjuvant and immunomodulator systems to better facilitate the development of a next generation of vaccines and immunotherapies. The present invention addresses these and other related needs.

BRIEF SUMMARY OF THE INVENTION

The present invention provides, in one aspect, an immunomodulator comprising purified *P. gingivalis* LPS, where the lipid A portion of the LPS has a molecular negative mass ion of 1435 or 1449. The immunomodulator is useful for redirecting an immune response of a mammal against an antigen of interest. Such antigens include, but are not limited to, tumor antigens (e.g., Her2/neu), bacterial, viral, or self antigens, and involve conditions such as cancer, autoimmune diseases such as arthritis, multiple sclerosis, inflammatory diseases, asthma, and minimizing transplantation rejection. The immunomodulator composition can include the antigen of interest, or they can be administered separately. Additional immunomodulators can be included in the composition, such as, e.g., adjuvants, such as alum, incomplete Freund's adjuvant, MPL, and others.

In the immunomodulator compositions of the invention, typically the LPS having a negative mass ion of 1435 or 1449 m/z will be at least about 70% pure, sometimes at least about 80% pure, preferably at least 90% pure, more preferably at least about 95% pure, up to 99% or more pure preparations. The two different species of LPS, 1435 and 1449, are often found together in purified preparations of LPS. For convenience, the species will be referred to hereinafter as 1435/1449, it being understood that they can be used separately or together. In addition to the 1435/1449 LPS or lipid A preparations and mimetics thereof, the immunomodulator formulations can contain other components, such as pharmaceutically acceptable carriers, excipients, and the like.

In another aspect, the invention provides a method for stimulating a protective immune response against a tumor, pathogen or autoimmune antigen in a mammal. A mammal which has a tumor, infectious, or autoimmune disease, or is substantially at risk of developing a tumor, infection or autoimmune condition, is administered an antigen characteristic of and capable of eliciting an immune response to the respective tumor, pathogen or autoimmune antigen. The subject also receives an immunomodulator which comprises purified *P. gingivalis* LPS, where said LPS has a molecular negative mass ion of 1435/1449. The antigen and immunomodulator are administered in an amount sufficient to direct an immune response which protects against development of the tumor, pathogen, autoimmune disease, inflammatory response, or transplant rejection, or causes the tumor, infection or autoimmune condition, inflammatory response or transplant rejection to diminish. According to this aspect of the invention, the composition can be administered multiple times to the subject to direct the immune response to the benefit of the condition being treated. Typically each subsequent administration will be separated by at least one or two weeks, sometimes a month or more, depending on the antigen, the condition being treated or prevented, and other clinical variables. The adjuvant composition will be administered by intramuscular, intradermal, subcutaneous, mucosal, intravenous, or intratumoral injection.

According to this aspect of the invention, additional adjuvants may also be employed to stimulate the desired immune response. Such additional adjuvant can include, for example, alum, incomplete Freund's adjuvant, or other acceptable adjuvant which is capable of eliciting the desired immune response. The *P. gingivalis* 1435/1449 m/z LPS used in the adjuvant formulation will typically be at least 70% pure, more usually at least about 90% or even 95% or more pure.

When the mammal being treated according to the present invention for a tumor, such as Her2/neu, typically the mammal is already suffering from the tumor and further development is inhibited and lifespan may be substantially increased compared to untreated subjects. The tumor may not develop further, or may even regress following administration of the adjuvant system of the invention and appropriate antigen composition. In some cases, the mammal is susceptible to developing the tumor but has not yet been diagnosed as having the tumor, and the onset of said tumor in the mammal is delayed.

In yet another aspect of the invention, a method is provided for stimulating a protective immune response against a tumor in a mammal by administering an antigen and an adjuvant composition, wherein the adjuvant is purified *P. gingivalis* LPS with the lipid A portion having a molecular negative mass ion of 1690. The antigen is one which is characteristic of and capable of eliciting an immune response to said tumor. The adjuvant and antigen are administered in an amount sufficient to elicit an immune response which protects against development of the tumor in the mammal.

BRIEF DESCRIPTION OF THE DRAWINGS

FIG. 7 depicts TLR2 and TLR2 plus TLR1 activation with *P. gingivalis* LPS preparations. HEK 293 cells were transiently transfected with human mCD14 and either huTLR2 (A and B) or huTLR2 plus TLR1 (C and D), with (A and C) or without (B and D) huMD-2. Each transfection experiment also contained the NF-κB reporter (ELAM-1-firefly luciferase) and the transfection control (β-actin-*Renilla* luciferase). Cells were then stimulated with various concentrations of Pam3CSK4, a TLR2 agonist, and Pg LPS$_{1435/1449}$ (some cells were also stimulated with various concentrations of *E. coli* LPS [C and D]) for 4 h and lysed, and the amount of luciferase produced was determined. Values are reported as the fold increase of relative luciferase units (firefly luciferase/*Renilla* luciferase) compared to the nonstimulated control response, which was set at 1. The data presented represent the means and standard deviations from triplicate wells from one experiment and are representative of at least three separate experiments.

FIGS. 10A and 10B show that *P. gingivalis* LPS 1435/1449 antagonizes *E. coli* LPS-induction of E-selectin protein and mRNA expression in HUVEC. HUVEC cells were treated with the LPS in amounts as shown for 4 hours; E-selectin protein was then detected using specific antibodies. In parallel studies, total RNA was harvested and RT-PCR analysis was performed to detect E-selectin and β-actin mRNA expression. Resulting RT-PCR products (lower panels) were imaged and subjected to densitometric analysis. E-selectin mRNA expression was normalized to β-actin mRNA expression and the resulting values were expressed as fold E-selectin mRNA induction relative to the unstimulated control.

FIG. 11 depicts $^3$H-thymidine T-cell proliferation of splenocytes from LPS-vaccinated mice. Spleen cells from mice immunized with Her-2 Neu positive cells and either *E. coli* LPS, *P. gingivalis* 1435/1449 LPS, *P. gingivalis* 1690 LPS, or no LPS as a control were collected and labeled with $^3$H-thymidine. Spleen cells were then assessed for their proliferation response (as measure by radiolabel incorporation) to either Her2/Neu positive tumor cells (MMC) or Her-2/Neu negative tumor cells (ANV) or no cells as a control. Experiments were performed in triplicate on spleen cells from each mouse, four mice per group, and results are shown as the mean of 12 data points/group.

DETAILED DESCRIPTION OF THE INVENTION

Figure 1A:
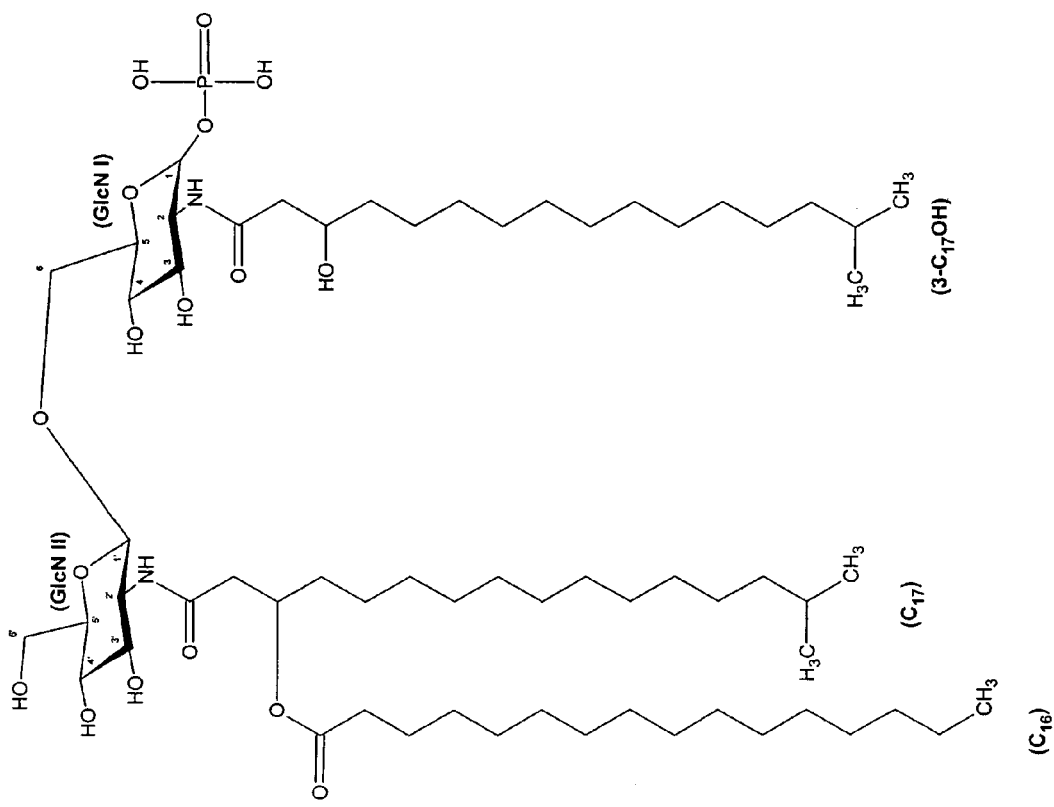
FIGS. 1A-1E depict the major characterized *P. gingivalis* lipid A mass ions.
Figure 1B:
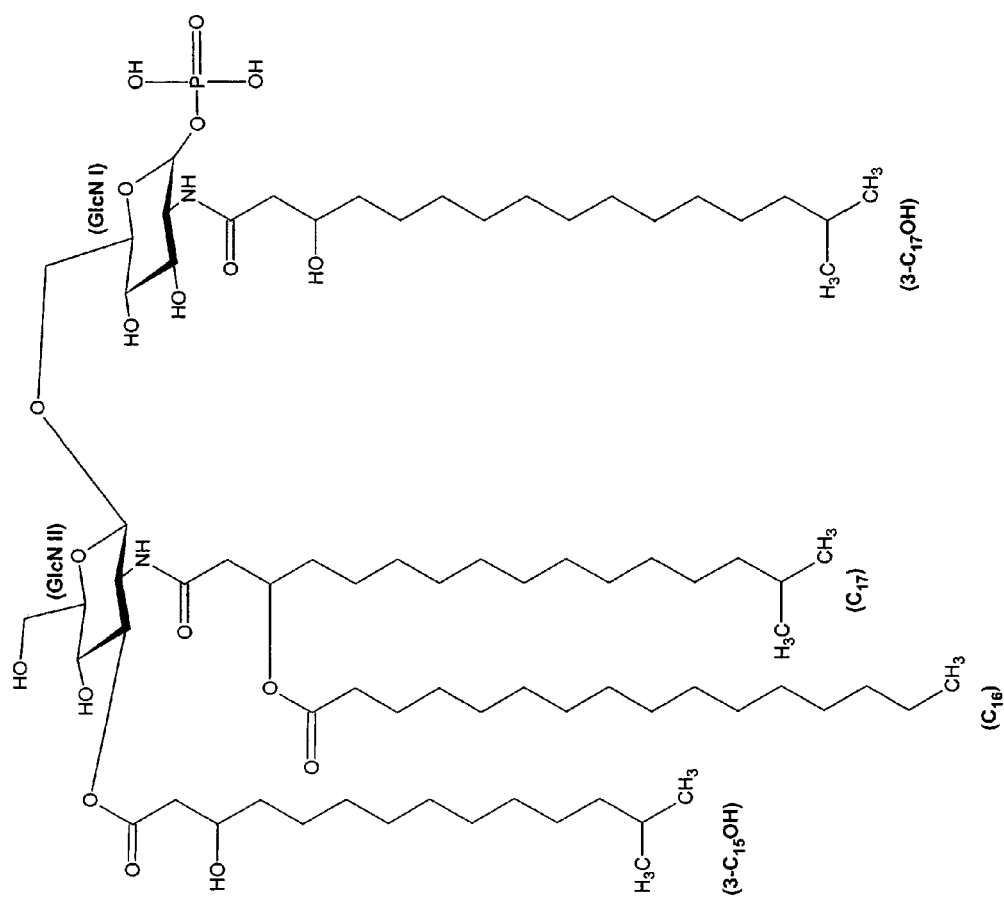
Figure 1C:
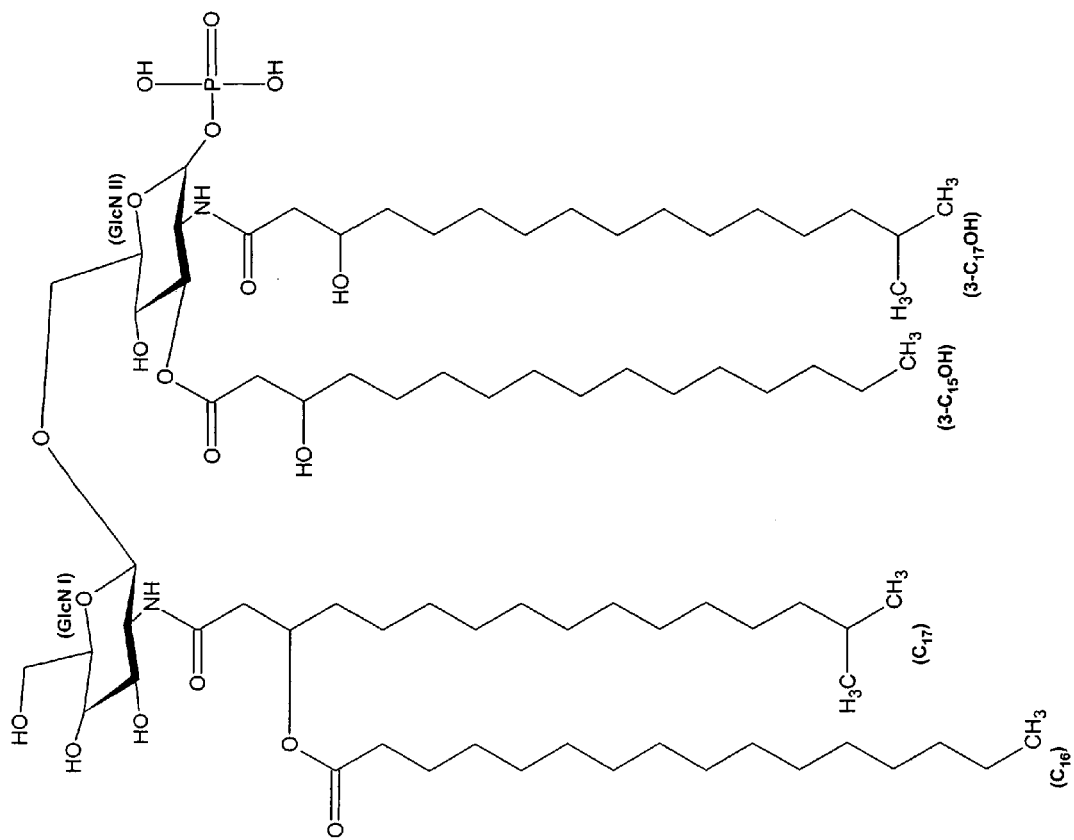

The present invention provides adjuvant compositions and methods for modulating an immune response of an animal using *P. gingivalis* LPS enriched for a fraction having a molecular negative mass ion of 1435/1449. The *P. gingivalis* 1435/1449 LPS is combined with an antigen preparation of interest, or is administered separately from the antigen, to stimulate or otherwise modulate the desired immune response. Additional immunomodulators, e.g., adjuvants, may be used with the *P. gingivalis* 1435/1449 LPS and antigen or may be separately administered. The antigen to which the immune response is elicited can be one or more of a variety of antigens targeted for a therapeutic or prophylactic response, and typically is, e.g., a tumor antigen, infectious disease antigen, autoimmune antigen, or MHC antigen.

*P. gingivalis* LPS contains multiple forms of lipid A, and in some cases the heterogeneity may be influenced by different media compositions, culture conditions, different bacterial strains, and extraction procedures employed. The most prevalent *P. gingivalis* LPS species contain lipid A mass ions at m/z 1195, 1435, 1449, 1690 and 1770 (FIG. 1). As used herein, *P. gingivalis* 1435/1449 LPS refers to a fraction that can be isolated from preparations of *P. gingivalis* LPS having a molecular negative mass ion of 1435 or 1449 when analyzed by matrix-assisted laser desorption-time of flight (MALDI-TOF) mass spectroscopy. Both free lipid A forms consist of a hydrophilic backbone consisting of beta(1,6)-linked D-glucosamine monosaccharide 1-phosphate. Both species have C16 acyl groups attached at the 3-OH group of the 2'-acyl group, C17i3-OH at position 2 of the reducing terminal residue, and position 2' of the nonreducing terminal unit is acylated with C17i-3OH, C16-3OH is found on m/z 1449 at position 3 or 3', while m/z 1435 has C15i-3OH at the 3 or 3' position. The *P. gingivalis* 1435/1449 as used herein thus refers to the 1435/1449 LPS fraction, lipid A obtained therefrom, detoxified lipid A, derivatives of the 1435/1449 lipid A, and mimetics of the 1435/1449 lipid A and LPS. By derivative is meant a compound that is structurally similar and possesses similar immunomodulating properties as the native compound. A derivative or mimetic may be a naturally occurring compound or prepared synthetically.

Bacteria processed with a 45% phenol extraction method, e.g., as described in Somerville et al., *J. Clin. Invest.* 97: 359-365 (1996), incorporated herein by reference, followed by generating lipid A from the LPS using the method of Caroff et al., *Carbohydr. Res.* 175: 273-282 (1988), incorporated herein by reference, provides a distinct negative mass ion species at 1690. This represents a penta-acylated monophosphorylated form of lipid A. Bacteria processed with a cold $MgCl_2$-ethanol method, e.g., according to the procedure of Darveau and Hancock, *J. Bacteriol.* 155:831-838 (1983), followed by lipid extraction (Folch et al., *J. Biol. Chem.* 226:497-509 (1957)) (both incorporated herein by reference) reveals three distinct negative mass ions using MALDI-TOF. One is a negative mass ion of 1195, representing a tri-acylated monophosphorylated form, and two other negative mass ions appear at 1435 and 1449 m/z, representing tetra-acylated monophosphorylated forms.

*P. gingivalis* LPS extraction using a commercially available reagent (Tri-Reagent; Yi and Hackett, *Analyst* 125:651-656 (2000)) and subsequent lipid A cleavage reveals numerous major lipid A mass ions clustered around m/z 1449, 1690, and 1770. The lipid A species found around each of these mass ions differed by smaller single methylene units (m/z 1420 and 1435 adjacent to 1449; 1675 adjacent to 1690; and 1705 and 1755 adjacent to 1770) and larger single methylene units (m/z 1465 and 1480 adjacent to 1449; 1705 adjacent to 1690; and 1785 and 1800 adjacent to 1770). This pattern of different lipid A mass ions is indicative of fatty acid chain length heterogeneity. In contrast, LPS extracted from whole cells by the $MgCl_2$-EtOH method was significantly reduced in both clusters of lipid A mass ions centered at m/z 1690 and m/z 1770, and had major lipid A mass ions at m/z 1435 and 1449. Two minor peaks at m/z 1420 and 1465 may be structurally related lipid A mass ions differing in fatty acid content.

In preparing an immunomodulating composition of the present invention, the *P. gingivalis* 1435/1449 LPS can be used modified or unmodified. In unmodified form, LPS is obtained from cultures of *P. gingivalis* such as, for example, ATCC 33277 or other strain deposited with the American Type Culture Collection or another depository. Strains of *P. gingivalis* can also be isolated clinically and identified using standard bacterial identification techniques. To obtain LPS, bacteria can be processed with a 45% phenol extraction method, supra, although for some strains this may not yield the 1435/1449 LPS. *P. gingivalis* processed with a cold $MgCl_2$-ethanol method, e.g., according to the procedure of Darveau and Hancock, supra, followed by lipid extraction (e.g., Folch et al., *J. Biol. Chem.* 226:497-509 (1957)), preferentially produces LPS enriched in negative mass ions at 1435 and 1449 m/z.

Lipid A is generated from the *P. gingivalis* LPS 1435/1449 using methods such as described in Caroff et al., *Carbohydr. Res.* 175: 273-282 (1988). Other methods also can be employed, such as, e.g., Qureshi and Takayama, *J. Biol. Chem.* 257:11808-15 (1982); and Hashimoto et al., *Int. Immunol.* 16:1431-1437 (2004), each incorporated herein by reference. If desired, the lipid A can be further detoxified by the procedures of, e.g., Rietschel et al., *FASEB J.* 8:217-225 (1994), incorporated herein by reference.

Thus, as discussed above, the present invention provides *P. gingivalis* 1435/1449 LPS isolated from its natural bacterial environment, substantially free of other LPS molecules, particularly *P. gingivalis* 1690 LPS. Substantially pure *P. gingivalis* 1435/1449 LPS of at least about 50% purity is preferred, at least about 70-80% purity more preferred, and 95-99% purity or more homogeneity most preferred, particularly for pharmaceutical and vaccine uses. Once purified, partially or to homogeneity, as desired, the *P. gingivalis* 1435/1449 LPS can then be used an immunomodulator, adjuvant or therapeutically, separately or as a component of a formulation, as described in more detail herein.

The present invention further provides pharmaceutical compositions comprising the immunomodulating compounds provided herein in admixture with one or more pharmaceutically acceptable carriers. Suitable carriers will depend on the condition being treated along with the route of administration. It will be understood that pharmaceutical compositions of the invention may be used as adjuvants to increase an immune response to an antigen or enhance certain activities of cells of the immune system, or in some instances as a prophylactic or therapeutic composition to prevent or treat a particular condition in a subject.

Thus, in one embodiment, the present invention provides pharmaceutical compositions containing a compound of the present invention and a pharmaceutically acceptable carrier. The compound is present in an amount effective to modulate an immune response, which is the amount of compound required to achieve the desired effect in terms of stimulating, inhibiting or directing a desired immune response, treating or inhibiting a disease or condition. The pharmaceutical compositions can also act as an adjuvant when co-administered with an antigen.

Compositions of this invention include both compositions that are formulated for direct administration of the active compounds to subjects without dilution, either in conjunction with a selected antigen, e.g., as a vaccine, or other active agent, or alone, as well as more concentrated compositions of the compounds that may be formulated for later dilution, so as to avoid shipment and/or storage of large amounts of diluent (e.g. water, saline or aqueous materials). In general, pharmaceutical compositions of this invention that are intended for direct or immediate administration to a subject (that is, without dilution) will contain one or more of the compounds, in a therapeutically effective amount. This amount will vary both based on the particular immunomodulator composition and on the therapeutic (or prophylactic) effect desired. More concentrated compositions will contain amounts of the immunomodulator composition of the invention as may be appropriate for such compositions.

For preparing pharmaceutical compositions containing a *P. gingivalis* 1435/1449 LPS immunomodulator of the invention, the pharmaceutically acceptable carriers can be either solid or liquid. Solid form preparations include powders, tablets, pills, capsules, cachets, suppositories, nanoparticles, time-release vehicles and dispersible granules. A solid carrier can be one or more substances which may also act as diluents, flavoring agents, binders, preservatives, tablet disintegrating agents, or an encapsulating material. In powders, the carrier is a finely divided solid which is in a mixture with the finely divided active component. In tablets, the active component is mixed with the carrier having the necessary binding properties in suitable proportions and compacted in the shape and size desired. Solid forms of the compositions also can be prepared by spray-drying aqueous formulations of the active immunomodulator (e.g. in the form of a salt) or by lyophilizing and milling with excipients.

Suitable carriers for the solid compositions of this invention include, for instance, magnesium carbonate, magnesium stearate, talc, sugar, lactose, pectin, dextrin, starch, gelatin, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it.

Liquid preparations of the immunomodulator compositions of the invention include solutions, suspensions, and emulsions, for example, water or water/propylene glycol solutions. For parenteral injection, liquid preparations can be formulated in solution in aqueous polyethylene glycol solution. In certain embodiments, the pharmaceutical compositions are formulated in a stable emulsion formulation (e.g., a water-in-oil emulsion or an oil-in-water emulsion) or an aqueous formulation that preferably comprise one or more surfactants. Suitable surfactants well known to those skilled in the art may be used in such emulsions. In one embodiment, the composition is in the form of a micellar dispersion comprising at least one suitable surfactant. The surfactants useful in such micellar dispersions include phospholipids. Examples of phospholipids include: diacyl phosphatidyl glycerols, such as: dimyristoyl phosphatidyl glycerol (DPMG), dipalmitoyl phosphatidyl glycerol (DPPG), and distearoyl phosphatidyl glycerol (DSPG); diacyl phosphatidyl cholines, such as: dimyristoyl phosphatidylcholine (DPMC), dipalmitoyl phosphatidylcholine (DPPC), and distearoyl phosphatidylcholine (DSPC); diacyl phosphatidic acids, such as: dimyristoyl phosphatidic acid (DPMA), dipalmitoyl phosphatidic acid (DPPA), and distearoyl phosphatidic acid (DSPA); and diacyl phosphatidyl ethanolamines such as: dimyristoyl phosphatidyl ethanolamine (DPME), dipalmitoyl phosphatidyl ethanolamine (DPPE), and distearoyl phosphatidyl ethanolamine (DSPE). Other examples include, but are not limited to, derivatives of ethanolamine (such as phosphatidyl ethanolamine, as mentioned above, or cephalin), serine (such as phosphatidyl serine) and 3'-O-lysyl glycerol (such as 3'-O-lysyl-phosphatidylglycerol).

Aqueous suspensions of the immunomodulator composition suitable for oral use can be made by dispersing the finely divided immunomodulator component in water with viscous material, such as natural or synthetic gums, resins, methylcellulose, sodium carboxymethylcellulose, and other well-known suspending agents. Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Thus, the immunomodulator systems of the invention are particularly advantageous in making and using vaccine and other immunostimulant compositions to treat or prevent diseases, such as inducing active immunity towards antigens in mammals, preferably in humans. Vaccine preparation is a well developed art and general guidance in the preparation and formulation of vaccines is readily available from any of a variety of sources.

The immunomodulator system of the present invention exhibits strong immunomodulating effects when administered over a wide range of dosages and a wide range of ratios. The amount of immunomodulator administered in conjunction with a vaccine dose is generally selected as an amount which together with the vaccine induces an immunoprotective response without significant adverse side effects in typical vaccines. Such amount will also vary depending upon which specific immunomodulators and immunogens are employed and how they are presented. Generally, it is expected that each dose will comprise about 1-1000 µg of antigen and 1-100 µg of immunomodulator, most typically about 2-100 µg of antigen and 150 µg of immunomodulator, and preferably about 5-50 µg of antigen preparation and 1-25 µg of immunomodulator. Of course, the dosages administered may be dependent upon the age, weight, kind of concurrent treatment, if any, and nature of the antigen and immunomodulator being administered.

The immunomodulator system of the invention can be used in conjunction with vaccine preparations derived and/or isolated from a wide variety of sources. These preparations include antigens for inducing immune responses to antigens derived from an infectious disease, autoimmune disease, tumor, or other disease that is to be treated with a given vaccine composition. By way of illustration, tumor antigens are used in vaccines with the immunomodulator compositions of the present invention for the prophylaxis and/or therapy of cancer. Cancer cells often have distinctive antigens on their surfaces, such as truncated epidermal growth factor, folate binding protein, epithelial mucins, melanoferrin, carcinoembryonic antigen (CEA), prostate-specific membrane antigen (PSMA), HER2-neu, and others. Tumor antigens will include all potentially antigenic molecules, not limited to proteins, but also to include other molecules such as carbohydrates, fats, and nucleotides (including RNA and DNA) or combinations of the above including with or without proteins, either covalent or not. Because tumor antigens are "normal" or related to normal components of the body, the immune system often fails to mount an effective immune response against those antigens to destroy the tumor cells. To achieve such a response, the immunomodulator systems described herein can be utilized in conjunction with the antigen(s), whether isolated or as part of a cell which displays the antigens, e.g., inactivated or killed tumor cells, including autologous cells. As a result, this immunomodulator effect facilitates the production of antigen specific T cells which target those tumor cells carrying on their surface the tumor antigen(s) used for immunization. Illustrative cancer types for which this approach can be used include prostate, colon, breast, ovarian, pancreatic, brain, head and neck, melanoma, leukemia, lymphoma, etc.

As noted above, the vaccine antigens also can be derived from viral sources, such as influenza virus, feline leukemia virus, feline immunodeficiency virus, HIV-1, HIV-2, herpes simplex virus type 2, cytomegalovirus, hepatitis A, B, C or E, respiratory syncytial virus, human papilloma virus, rabies, measles, or hoof and mouth disease viruses. Vaccine antigens can also be derived from bacterial or protozoan sources, such as anthrax, diphtheria, Lyme disease, malaria, *M. tuberculosis*, *S. pneumoniae*, *H. influenza*, Leishmaniasis, *T. cruzi*, Ehrlichia, Candida etc.

The microbial-derived tumor antigen(s), like the tumor antigens, can be comprised of natural or synthetic amino acids, e.g., in the form of peptides, polypeptides, or proteins, polysaccharides, fats, nucleotides (including RNA and DNA) or can be mixtures thereof, covalent or not. Illustrative antigens can be isolated from natural sources, synthesized by means of solid phase synthesis, or can be obtained by way of recombinant DNA techniques.

In another embodiment, the antigen present in the vaccine compositions used with the immunomodulator system of the present invention is not a foreign antigen, rather it is a self antigen, e.g., the vaccine composition is directed toward an autoimmune disease such as type 1 diabetes, conventional organ-specific autoimmune diseases, neurological diseases, rheumatic diseases, psoriasis, connective tissue diseases, autoimmune cytopenias, and other autoimmune diseases. Such conventional organ specific autoimmunity may include thyroiditis (Graves+Hashimoto's), gastritis, adrenalitis (Addison's), ovaritis, primary biliary cirrhosis, myasthenia gravis, gonadal failure, hypoparathyroidism, alopecia, malabsorption syndrome, pernicious anemia, hepatitis, anti-receptor antibody diseases and vitiligo. Such neurological diseases may include schizophrenia, Alzheimer's disease, depression, hypopituitarism, diabetes insipidus, sicca syndrome and multiple sclerosis. Such rheumatic diseases/connective tissue diseases may include rheumatoid arthritis, systemic lupus erythematous (SLE) or Lupus, scleroderma, polymyositis, inflammatory bowel disease, dermatomyositis, ulcerative colitis, Crohn's disease, vasculitis, psoriatic arthritis, exfoliative psoriatic dermatitis, pemphigus vulgaris, Sjogren's syndrome. Other autoimmune related diseases may include autoimmune uvoretinitis, glomerulonephritis, post myocardial infarction cardiotomy syndrome, pulmonary hemosiderosis, amyloidosis, sarcoidosis, aphthous stomatitis, and other immune related diseases. In other embodiments the immunomodulator can be used with one or more selected MHC antigens of the tissue graft to prevent transplant rejection in a host, e.g., to inhibit or treat graft-versus-host disease.

In another embodiment of the invention, the immunomodulator system of the present invention can be administered alone, i.e., without a co-administered antigen, to potentiate the immune system for treatment of chronic infectious diseases, especially in immune compromised patients. Illustrative examples of infectious diseases for which this approach may be employed for therapeutic or prophylactic treatment can be found in U.S. Pat. No. 5,508,310, incorporated herein by reference. Potentiation of the immune system in this way can also be useful as a preventative measure to limit the risks of other infections, such as, e.g., nosocomial and/or post-surgery infections.

In another embodiment of the invention, the immunomodulator may also be used in combination with an antigen for in vitro or ex vivo vaccination including stimulating dendritic cells, B cells, T cells, and other immune effectors.

While any suitable carrier known to those of ordinary skill in the art may be employed in the immunomodulator compositions of this invention, the type of carrier will typically vary depending on the desired mode of intended administration. The immunomodulator compositions may be formulated for any appropriate manner of administration, including for example, topical, inhalational, oral, nasal, intravenous, intraperitoneal, intradermal, intratumoral, subcutaneous or intramuscular administration. For parenteral administration, such as subcutaneous injection, the carrier will often comprise water, saline, alcohol, a fat, a wax or a buffer. For oral administration, the above carriers are often used, or a solid carrier such as mannitol, lactose, starch, magnesium stearate, sodium saccharine, talcum, cellulose, glucose, sucrose, and magnesium carbonate, can also be employed. Biodegradable microparticles (e.g., polylactate polyglycolate or nanoparticles may also be employed as carriers for the compositions of this invention. Suitable biodegradable microspheres are disclosed, for example, in U.S. Pat. Nos. 4,897,268; 5,075,109; 5,928,647; 5,811,128; 5,820,883; 5,853,763; 5,814,344 and 5,942,252, incorporated herein by reference. Modified hepatitis B core protein carrier systems are also suitable, such as those described in WO 99/40934, and references cited therein, incorporated herein by reference. One can also employ a carrier comprising particulate-protein complexes, such as those described in U.S. Pat. No. 5,928,647, incorporated herein by reference in its entirety, which are capable of inducing class I-restricted CTL responses in a host.

In one illustrative embodiment, the vaccine formulations are administered to the mucosae, in particular to the oral cavity, and preferably to a sublingual site, for eliciting an immune response. Oral cavity administration may be preferred in many instances over traditional parenteral delivery due to the ease and convenience offered by noninvasive administration techniques. Moreover, this approach further provides a means for eliciting mucosal immunity, which can often be difficult to achieve with traditional parenteral delivery, and which can provide protection from airborne pathogens and/or allergens. An additional advantage of oral cavity administration is that patient compliance may be improved with sublingual vaccine delivery, especially for pediatric applications, or for applications traditionally requiring numerous injections over a prolonged period of time, such as with allergy desensitization therapies.

The immunomodulator compositions can also comprise buffers (e.g., neutral buffered saline, phosphate buffered saline or phosphate buffers w/o saline), carbohydrates (e.g., glucose, mannose, sucrose or dextrans), mannitol, proteins, polypeptides or amino acids such as glycine, antioxidants, bacteriostats, chelating agents such as EDTA or glutathione, immunomodulators (e.g., aluminum hydroxide), solutes that render the formulation isotonic, hypotonic or weakly hypertonic with the blood of a recipient, suspending agents, thickening agents and/or preservatives. Alternatively, compositions of the present invention may be formulated as a lyophilizate. The compositions can also be encapsulated within liposomes using well established technology.

In another embodiment, the composition is an emulsion, such as a water-in-oil emulsion or an oil-in-water emulsion. The preparation of such emulsions are generally well known to those skilled in this art.

The immunomodulator system of the present invention can be employed as the sole immunomodulator system, or alternatively, can be administered together with other immunomodulators or immunoeffectors. By way of illustration, such immunomodulators can include oil-based adjuvants (for example, Freund's Complete and Incomplete), liposomes, mineral salts (for example, $AlK(SO_4)_2$, $AlNa(SO_4)_2$, $AlNH_4(SO_4)$, silica, alum, $Al(OH)_3$, $Ca_3(PO_4)_2$, kaolin and carbon), polynucleotides (for example, poly IC and poly AU acids), polymers (for example, non-ionic block polymers, polyphosphazenes, cyanoacrylates, polymerase-(DL-lactide-co-glycoside), among others, and certain natural substances (wax D from *M. tuberculosis*, as well as substances found in *C. parvum*, *B. pertussis*, and members of the genus *Brucella*), bovine serum albumin, diphtheria toxoid, tetanus toxoid, edestin, keyhole-limpet hemocyanin, and eukaryotic proteins such as interferons, interleukins, or tumor necrosis factor. Such proteins may be obtained from natural or recombinant sources according to methods known to those skilled in the art. When obtained from recombinant sources, the immunomodulator may comprise a protein fragment comprising at least the immunostimulatory portion of the molecule. Other known immunostimulatory macromolecules which can be used in the practice of the invention include, but are not limited to, polysaccharides, tRNA, non-metabolizable synthetic polymers such as polyvinylamine, polymethacrylic acid, polyvinylpyrrolidone, mixed polycondensates (with relatively high molecular weight) of 4',4-diaminodiphenyl-methane-3,3'-dicarboxylic acid and 4-nitro-2-aminobenzoic acid (See Sela, *Science* 166:1365-1374 (1969)) or glycolipids, lipids or carbohydrates.

In one embodiment, the immunomodulator system is designed to also induce an immune response that includes the Th1 type. High levels of Th1-type cytokines (e.g., IFN-gamma., TNF-alpha., IL-2 and IL-12) tend to favor the induction of cell mediated immune responses to an administered antigen. In other embodiments, high levels of Th2-type cytokines (e.g., IL-4, IL-5, IL-6 and IL-10) tend to favor the induction of humoral immune responses. Within a preferred embodiment, in which a response is predominantly Th2-type, the level of Th2-type cytokines will increase to a greater extent than the level of Th1-type cytokines. The levels of these cytokines may be readily assessed using standard assays. For a review of the families of cytokines, see Mosmann and Coffinan, *Ann. Rev. Immunol.* 7:145-173, 1989.

For example, additional immunomodulators for use in eliciting a predominantly Th1-type response include, for example, an aluminum salt, or CpG-containing oligonucleotides (in which the CpG dinucleotide is unmethylated). Such oligonucleotides are well known and are described, for example, in WO 96/02555, WO 99/33488 and U.S. Pat. Nos. 6,008,200 and 5,856,462. Immunostimulatory DNA sequences are also described, for example, by Sato et al., *Science* 273:352, 1996. Other illustrative adjuvants that can be included in the compositions include Montanide ISA 720 (Seppic, France), SAF (Chiron, Calif., United States), ISCO-MATRIX® (a saponin-based adjuvant from CSL, Limited), and MF-59 (Chiron).

The compositions described herein may be administered as part of a sustained release formulation (i.e., a formulation such as a capsule, sponge or gel (composed of polysaccharides, for example) that effects a slow release of immunomodulator compound following administration). Such formulations may generally be prepared using well known technology (see, e.g., Coombes et al., *Vaccine* 14:1429-1438, 1996) and administered by, for example, oral, rectal or subcutaneous implantation, or by implantation at the desired target site. Sustained-release formulations may also contain an antigen of interest dispersed in a carrier matrix and/or contained within a reservoir surrounded by a rate controlling membrane. Carriers for use within such formulations are biocompatible, and may also be biodegradable; preferably the formulation provides a relatively constant level of immunomodulator and antigen component release. Such carriers include microparticles of poly(lactide-co-glycolide), polyacrylate, latex, starch, cellulose, dextran and the like. Other delayed-release carriers include supramolecular biovectors, which comprise a non-liquid hydrophilic core (e.g., a cross-linked polysaccharide or oligosaccharide) and, optionally, an external layer comprising an amphiphilic compound, such as a phospholipid (see e.g., U.S. Pat. No. 5,151,254 and WO 94/20078, WO/94/23701 and WO 96/06638). The amount of immunomodulator and optionally antigen compound contained within a sustained release formulation will vary depending upon the site of implantation, the rate and expected duration of release and the nature of the condition to be treated or prevented.

Any of a variety of known delivery vehicles may be employed within pharmaceutical compositions and vaccines to facilitate production of an antigen-specific immune response that targets cells. Delivery vehicles include antigen presenting cells (APCs), such as dendritic cells, macrophages, B cells, monocytes and other cells that may be engineered to be efficient APCs. Such cells may, but need not, be genetically modified to increase the capacity for presenting the antigen, to improve activation and/or maintenance of the T cell response, to have anti-target effects per se and/or to be immunologically compatible with the receiver (i.e., matched HLA haplotype). APCs may generally be isolated from any of a variety of biological fluids and organs, including tumor and peri-tumoral tissues, and may be autologous, allogeneic, syngeneic or xenogeneic cells.

Certain embodiments of the present invention use dendritic cells or progenitors thereof as antigen-presenting cells. Dendritic cells are highly potent APCs (Banchereau and Steinman, *Nature* 392:245-251 (1998)) and have been shown to be effective as a physiological adjuvant for eliciting prophylactic or therapeutic anti-tumor immunity (Timmerman and Levy, *Ann. Rev. Med.* 50:507-529 (1999)). In general, dendritic cells may be identified based on their typical shape (stellate in situ, with marked cytoplasmic processes (dendrites) visible in vitro), their ability to take up, process and present antigens with high efficiency and their ability to activate naive T cell responses. Dendritic cells may, of course, be engineered to express specific cell-surface receptors or ligands that are not commonly found on dendritic cells in vivo or ex vivo, and such modified dendritic cells are contemplated for use in the present invention. As an alternative to dendritic cells, secreted vesicles antigen-loaded dendritic cells (called exosomes) may be used within a vaccine. Another alternative to dendritic cells is dendritic cell/tumor cell fusion vaccines.

Dendritic cells and progenitors may be obtained from peripheral blood, bone marrow, tumor-infiltrating cells, peritumoral tissue-infiltrating cells, lymph nodes, spleen, skin, umbilical cord blood or any other suitable tissue or fluid. For example, dendritic cells may be differentiated ex vivo by adding a combination of cytokines such as GM-CSF, IL-4, IL-13 and/or TNFα to cultures of monocytes harvested from peripheral blood. Alternatively, CD34 positive cells harvested from peripheral blood, umbilical cord blood or bone marrow may be differentiated into dendritic cells by adding to the culture medium combinations of GM-CSF, IL-3, TNF.alpha., CD40 ligand, LPS, flt3 ligand and/or other compound(s) that induce differentiation, maturation and proliferation of dendritic cells.

APCs may generally be transfected with a polynucleotide encoding an antigen polypeptide (or portion or other variant thereof) such that the antigen polypeptide, or an immunogenic portion thereof is expressed any where in or on the cells or elaborated from the cell. Such transfection may take place ex vivo, and a composition or vaccine comprising such transfected cells, and the immunomodulators described herein, may then be used for therapeutic purposes. Antigen loading of dendritic cells may be achieved by incubating dendritic cells or progenitor cells with the antigen polypeptide, DNA (naked or within a plasmid vector) or RNA; or with antigen-expressing recombinant bacterium or viruses (e.g., vaccinia, fowlpox, adenovirus or lentivirus vectors). Prior to loading, the polypeptide may be covalently conjugated to an immunological partner that provides T cell help (e.g., a carrier molecule). The dendritic cell is administered to the patient in conjunction with the immunomodulator of the invention described herein.

The following examples are intended to illustrate but not limit the invention.

EXAMPLES

Example 1

P. gingivalis 1690 LPS

P. gingivalis strain 33277 was obtained from American Type Culture Collection. It was examined for purity, re-identified, and stored at −70° C. Cultures were made from frozen bacterial stocks to avoid repetitive subculture. Bacterial cells were grown for LPS isolation as follows: P. gingivalis was grown anaerobically at 37° C. for 24 hours in an enriched trypticase soy broth (30 gm/liter) containing yeast extract (Difco) 1 gm/liter; glucose 1 gm/liter; potassium nitrate 0.5 gm/liter; sodium lactate (Sigma L-1375) 1 ml/liter; sodium succinate 0.5 gm/liter; sodium fumarate 1 gm/liter; after autoclaving, filter-sterilized supplements were added (sodium carbonate 0.4 gm/liter; hemin (Sigma H-2250) 0.005 gm/liter; cysteine 0.4 gm/liter; and vitamin K (Sigma M-5625) 0.001 gm/liter). Stationary phase cells were employed for LPS isolation.

Bacteria were harvested by centrifugation and lyophilized. Bacteria were processed with the 45% phenol extraction method described in Somerville et al., *J. Clin. Invest.* 97: 359-365 (1996), incorporated herein by reference.

Figure 1D:
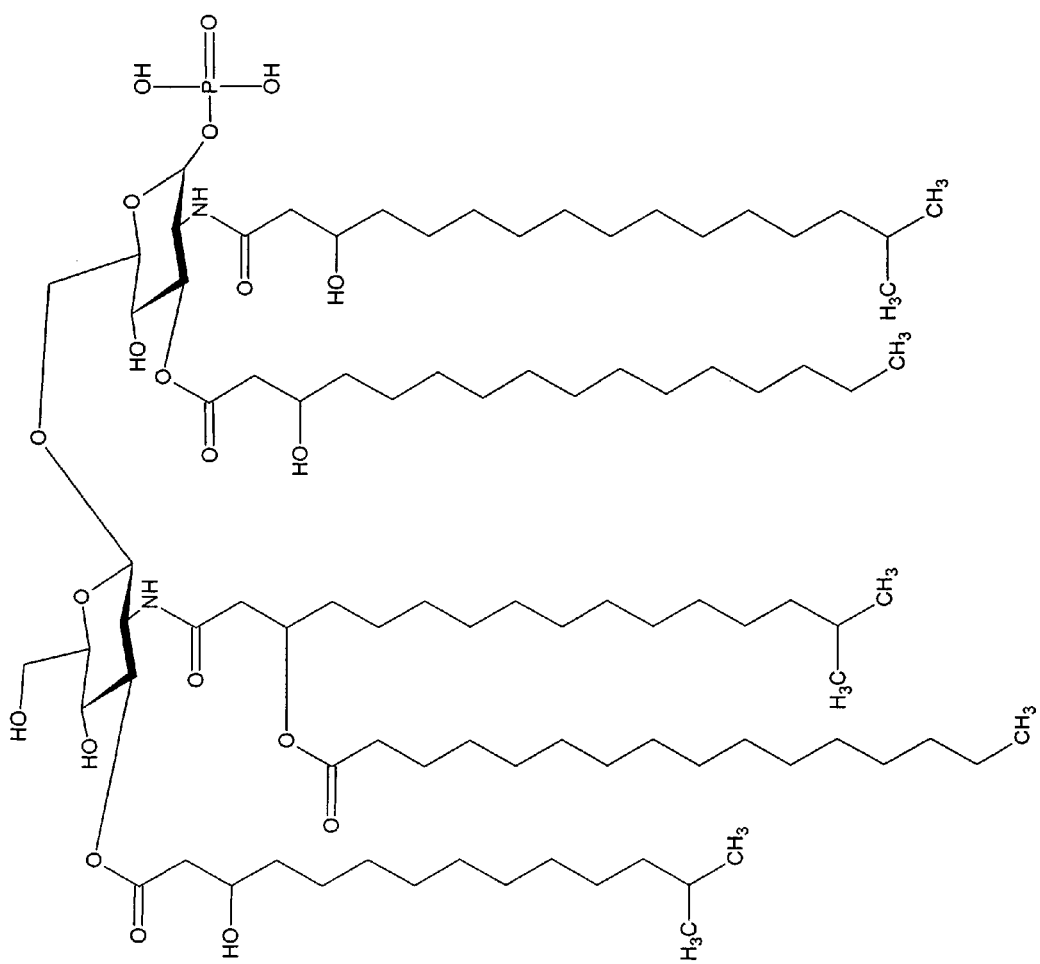
Figure 1E:
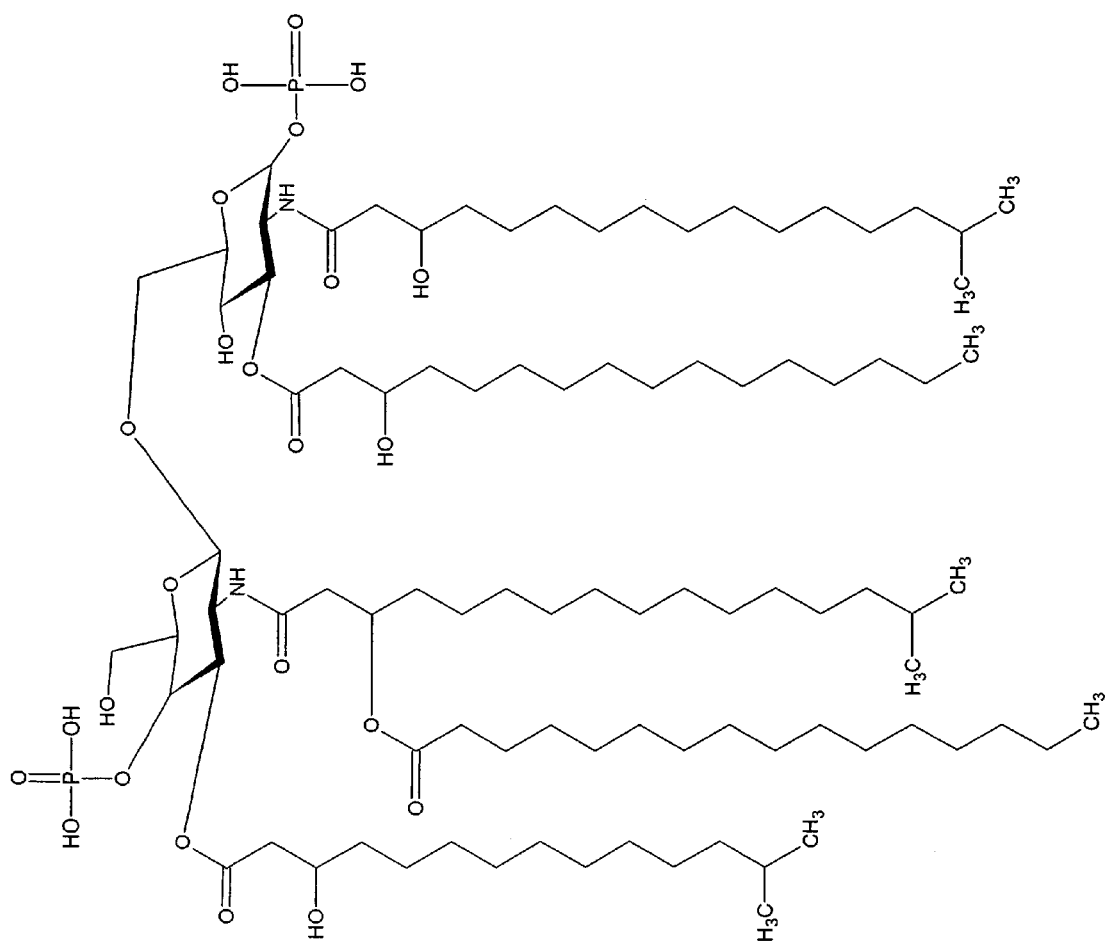

Lipid A was generated from the LPS of *P. gingivalis* using the method of Caroff et al., *Carbohydr. Res.* 175: 273-282 (1988), incorporated herein by reference. Using MALDI-TOF, a distinct negative mass ion at 1690 was observed. Kumada et al., *J. Bacteriol* 177:2098-2106 (1995). As shown in FIG. 1D, this represents a penta-acylated monophosphorylated form.

Biologic Activity of *P. gingivalis* 1690 LPS

Figure 2:
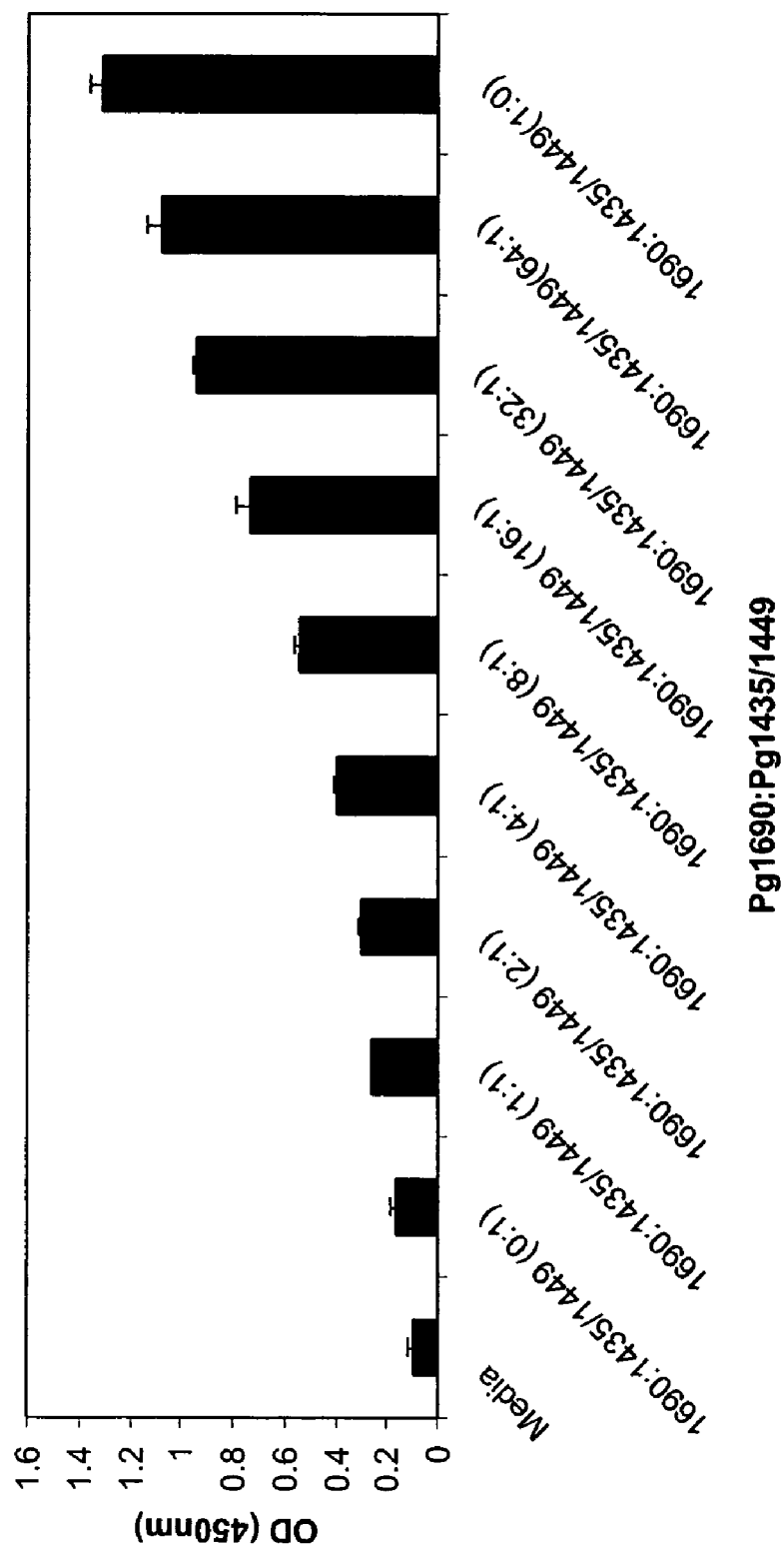
FIG. 2 shows that highly purified *P. gingivalis* 1435/1449 LPS even at a 1:64 ratio (1435/1449: 1690) can antagonize *P. gingivalis* 1690 LPS from activating HUVEC E-selectin.

The biologic response of the purified LPS was tested for E-selectin expression on HUVEC cells according to the method of Darveau et al., *Infect. Immun.* 63:1311-1317 (1995). These cells normally produce E-selectin in response to *E. coli* or its purified LPS. The purified *P. gingivalis* 1690 LPS stimulated E-selectin expression and was able to stimulate TNF-α from stimulated MonoMac 6 cells (ACC 124, German Collection of Microorganisms and Cell Cultures, Braunschweig, Germany). FIG. 2 shows that this fraction is also inhibited from stimulating E-selectin by the 1435/1449 fractions (described below), even at a ratio of 1:64 (1435/1449:1690).

Example 2

P. gingivalis 1435/1449 LPS

P. gingivalis bacteria were cultivated as described for Example 1 above and harvested by centrifugation and lyophilized. Bacteria were processed with the cold MgCl$_2$-ethanol method according to the procedure of Darveau and Hancock, *J. Bacteriol.* 155:831-838 (1983), followed by lipid extraction. Folch et al., *J. Biol. Chem.* 226:497-509 (1957). The LPS was further purified to remove trace endotoxin protein by the method of Manthey and Vogel. *J. Endotox. Res.* 1:84-91 (1994).

Biochemical Analysis of Purified Lipid A.

Figure 3:
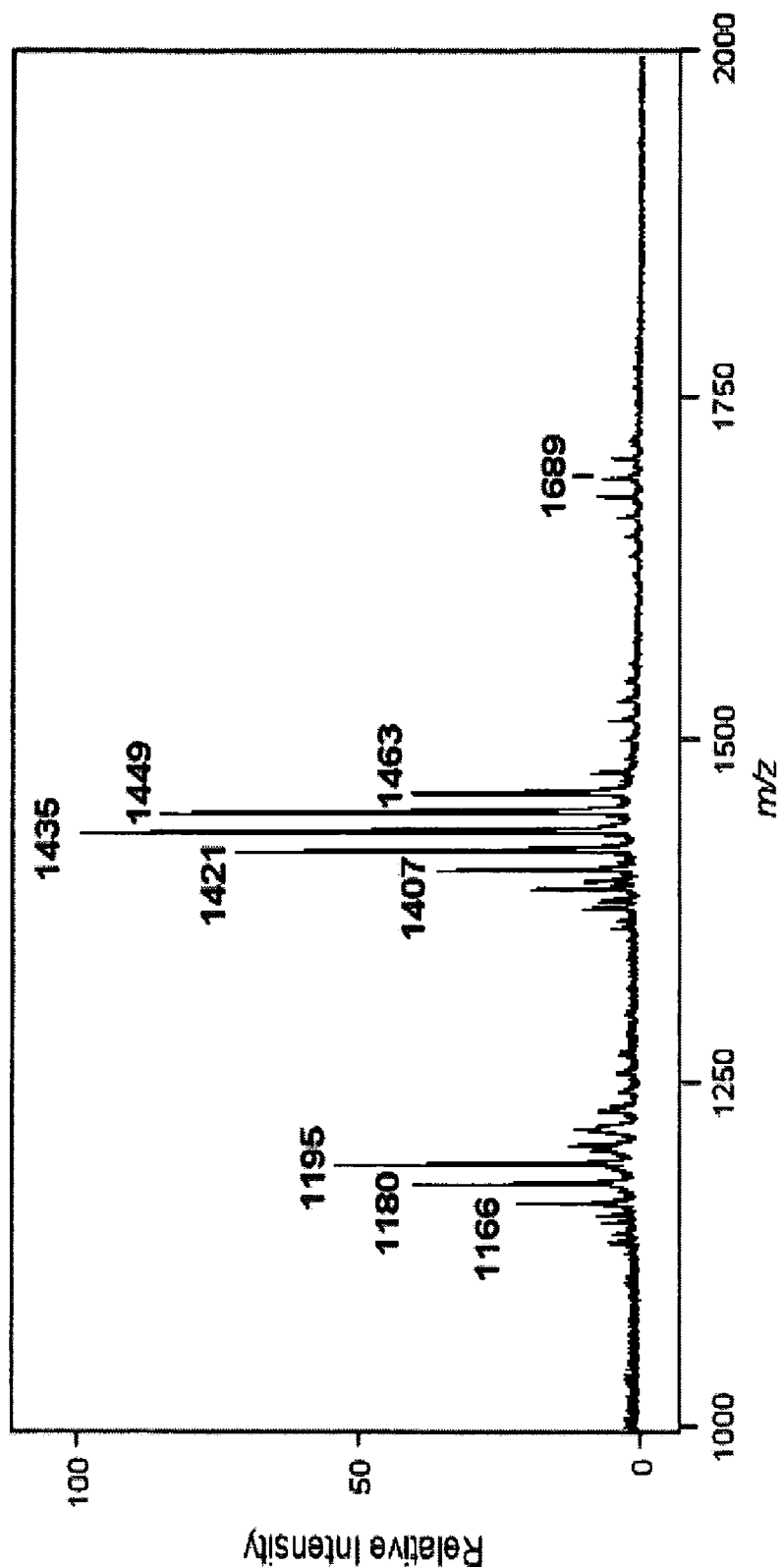
FIG. 3 depicts MALDI-TOF analysis of MgCl$_2$-purified *P. gingivalis* LPS lipid A.

Lipid A was generated from the LPS of *P. gingivalis* using the method of Caroff et al., *Carbohydr. Res.* 175: 273-282 (1988). Using MALDI-TOF, three distinct negative mass ions were observed, as seen in FIG. 3. Ogawa, *FEBS Lett.* 332: 197-201 (1993); Kumada et al., *J. Bacteriol.* 177:2098-2106 (1995). One is a negative mass ion of 1195, representing a tri-acylated monophosphorylated form (FIG. 1A). Two other negative mass ions at 1435 (FIG. 1B) and 1449 (FIG. 1C), represented tetra-acylated monophosphorylated forms.

Biologic Activity of *P. gingivalis* LPS

The biologic response of the purified LPS was tested for E-selectin expression on HUVEC cells according to the method of Darveau et al., *Infect. Immun.* 63:1311-1317 (1995). As described above, these cells normally produce E-selectin in response to *E. coli* or its purified LPS. The purified *P. gingivalis* LPS did not stimulate E-selectin expression, and inhibited *E. coli* LPS-mediated stimulation.

Example 3

Conversion of P. gingivalis Agonist 1690 LPS to Antagonist 1195 LPS

P. gingivalis bacteria were cultivated as described for Example 1 above and harvested by centrifugation and lyophilized. Bacteria were processed with the 45% phenol extraction method described in Somerville et al., *J. Clin. Invest.* 97: 359-365 (1996).

Biochemical Analysis of Purified Lipid A.

Lipid A was generated from the LPS using the method of Caroff et al., *Carbohydr. Res.* 175: 273-282 (1988). Using MALDI-TOF, a distinct negative mass ion at 1690 was observed. This represented a penta-acylated monophosphorylated form. This lipid A preparation was then subjected to concentrated NH$_4$OH for 18 hours at room temperature. MALDI-TOF analysis showed that the 3 and 3' acyl and acyloxyacyl esters (but not linked fatty acids) were cleaved resulting in a m/z of 1195. Some residual m/z 1690 remained, and an unidentified m/z of 1440 which was present in the parent extract as well and appeared to be impervious to NH$_4$OH treatment.

Biologic Activity of *P. gingivalis* LPS

Figure 4:
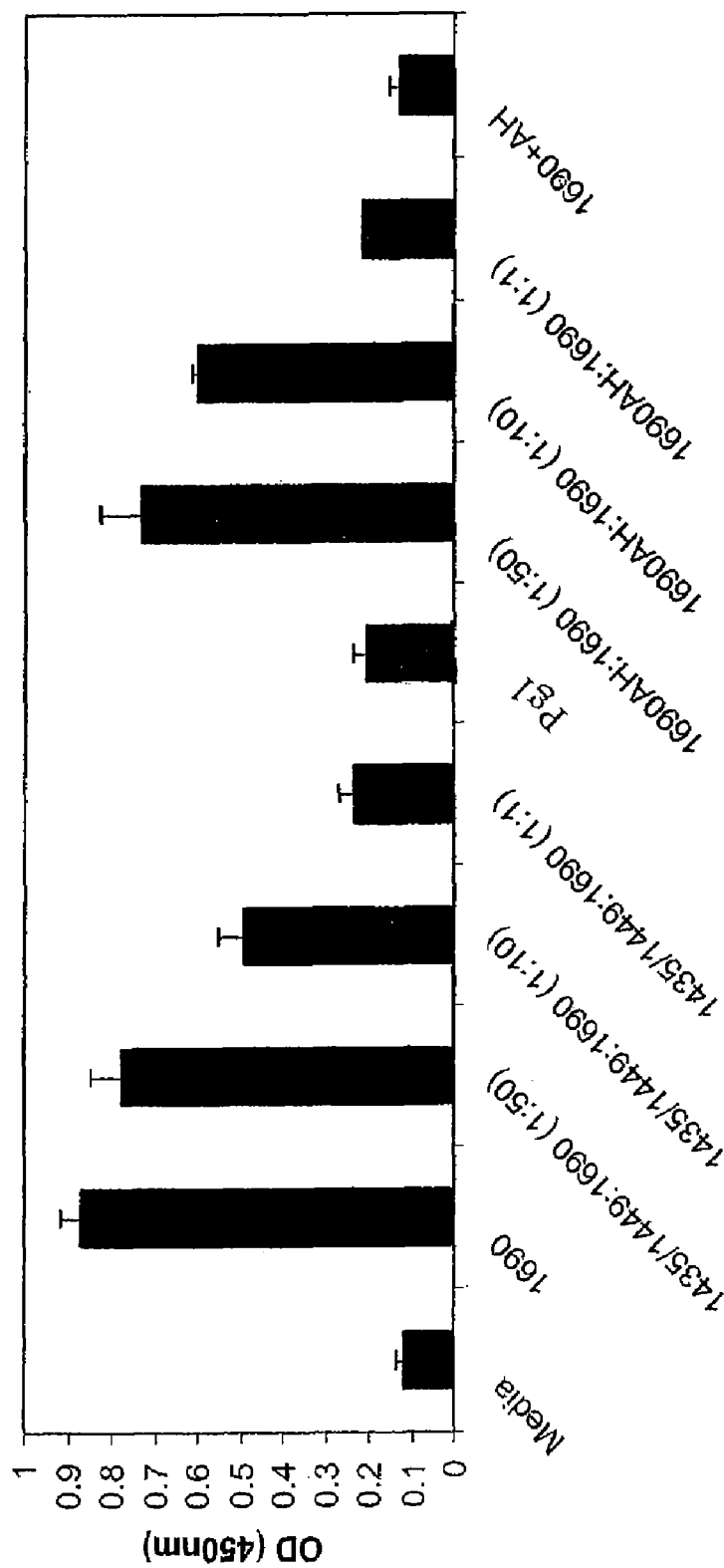
FIG. 4 shows that the m/z 1690 LPS preparation stimulated E-selectin expression whereas the preparation containing m/z 1195 LPS fraction (1690+AH, ammonium hydroxide) did not. This fraction of 1690+AH inhibited the m/z 1690 preparation from stimulating E-selectin expression much the same as a preparation containing 1435/1449, shown in the Fig. as Pg1). This shows that when 1690 LPS is treated with ammonium hydroxide, it cleaves the 1690 structure to yield the 1195 species, and this species antagonizes 1690 as does the 1435/1449 fraction.

LPS containing m/z 1195 was prepared from the m/z parent preparation using concentrated NH$_4$OH for 18 hours at room temperature as described above. The biologic response of the m/z 1195 and 1690 fractions were tested for E-selectin expression on HUVEC cells as described in Example 1 above. These cells normally produce E-selectin in response to m/z 1690 preparations. FIG. 4 shows that the m/z 1690 LPS preparation stimulated E-selectin expression but, in contrast, the preparation of m/z 1195 did not stimulate E-selectin expression. Furthermore, the m/z 1195 fraction actually inhibited the m/z 1690 preparation from stimulating E-selectin expression, much the same as the 1195 and 1435/1449 preparations described above.

Example 4

Inhibiting Tumor Induction Using P. gingivalis LPS as an Immunomodulator

P. gingivalis LPS 1690 and 1435/1449 preparations were tested as immunomodulators in a vaccine to block tumor development. A biologically-relevant mouse model of human breast cancer, the neu-transgenic (neu-tg) mouse, was used. The neu-tg mouse carries rat neu as a transgene driven by the MMTV promoter, which results in expression of the transgene in the breast epithelium. The development of breast cancer in these animals is similar to that in humans, progressing from hyperplasia (evident at 30 weeks of age) to invasive metastatic breast cancer by 50-60 weeks of age. A tumor cell line, MMC, was established from a spontaneous tumor lesion to use for tumor challenge and whole cell vaccine experiments.

Mouse Tumor Model

Neu-transgenic mice (strain name, FVB/N-TgN (MMTV-neu)-202Mul) were obtained from Jackson Laboratories (Bar Harbor, Me.). The mice have non-mutated, non-activated rat neu under control of the mouse mammary tumor virus (MMTV) promoter. This is parallel to human HER-2/neu-overexpressing cancer, in that expression of neu under the mouse mammary tumor virus promoter results in amplified expression in the breast epithelium. This is analogous to gene amplification in humans that results in over-expression of the non-mutated HER-2/neu gene with a significant proportion of cases expressing medium to high levels of the protein.

Tumor Cell Line

A mouse mammary carcinoma (MMC) cell line was established from a spontaneous tumor harvested from the neu-transgenic mice. MMC cells were grown and maintained in RPMI 1640 supplemented with 20% FCS as well as penicillin/streptomycin and L-glutamine. Approximately $5 \times 10^6$ irradiated cells were used on day 1 of vaccination while $2 \times 10^6$ irradiated cells were used on day 14 of vaccination. For live cell induction, $2 \times 10^6$ cells were used on day 28.

Vaccination Protocol and Tumor Cell Induction

The vaccination protocol was as follows: Four vaccine groups were tested with three animals in each group. The mice received *P. gingivalis* 1690 LPS; *P. gingivalis* 1435/1449 LPS; *E. coli* LPS (ATCC strain 25922; LPS purified using phenol as described for *P. gingivalis* 1690 LPS or MgCl$_2$ for 1435/1449 as described above); or no LPS.

Mice were vaccinated subcutaneously with a composition containing $5 \times 10^6$ irradiated (15,000 rad) HER-2/neu tumor cells as the antigen, 25 μg LPS as the immunomodulator/adjuvant (or no LPS in the control group), and incomplete Freund's adjuvant (IFA) [1:1 mix]. The IFA constituted 50% of the vaccine volume (100 μl).

Fourteen days later the vaccination was repeated with $5 \times 10^6$ irradiated HER-2/neu tumor cells as the antigen, 25 μg LPS from *E. coli*, *P. gingivalis* 1435/1449, or *P. gingivalis* 1690, and IFA.

Fourteen days following the second vaccination, mice were injected with $5 \times 10^6$ live tumor cells at a site distant to the vaccination site. At this dose of live MMC tumor cells, tumors will develop 100% of the time unless otherwise inhibited. Mice were then checked every 3-4 days for tumor development. When tumors were detected they were measured in three dimensions.

Figure 5A:
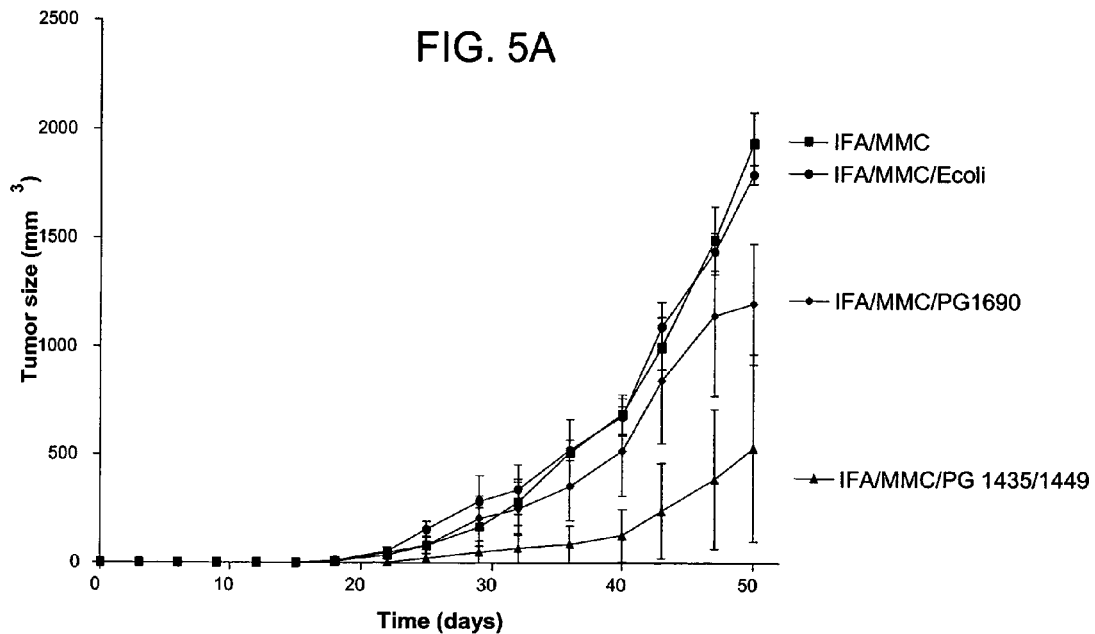
FIG. 5A shows that the vaccine containing *P. gingivalis* 1435/1449 was the most effective at slowing the growth of tumors, compared to the somewhat effective vaccine containing 1690 m/z fraction, and the controls containing no LPS or *E. coli* LPS.
Figure 5B:
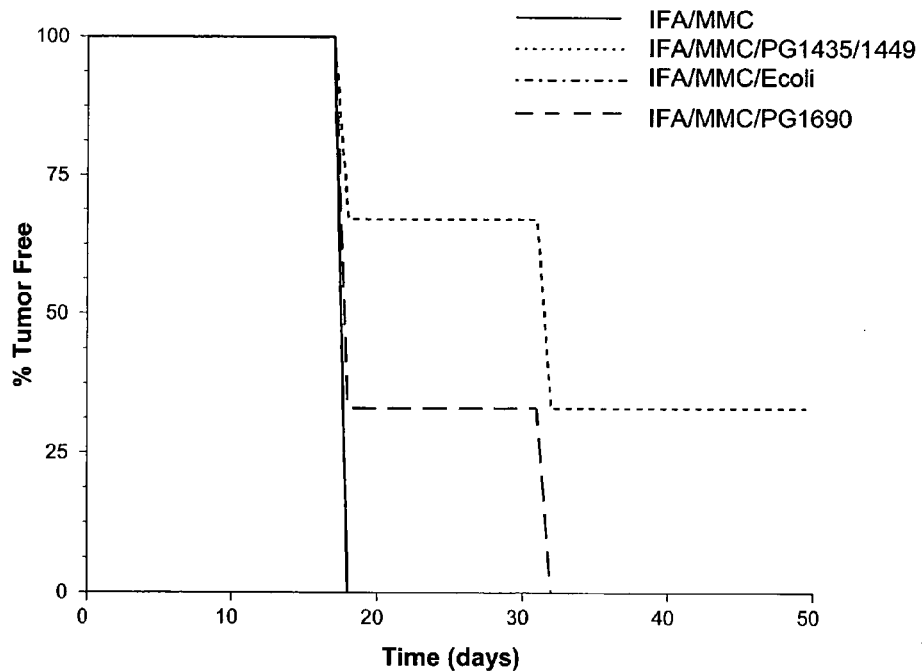
FIG. 5B shows that the vaccine containing *P. gingivalis* 1435/1449 was the most effective at delaying the onset of tumors, compared to the less effective vaccine containing 1690 m/z fraction, whereas *E. coli* LPS had no impact on tumor size when compared to control mice receiving IFA and irradiated tumor cells alone, where 100% of the animals rapidly developed large tumors.

The results, depicted in FIG. 5B, show that 100% of animals receiving IFA alone, and mice injected with *E. coli* LPS, developed tumors by eighteen days after injection with live tumor cells. In contrast, injections of vaccine preparations containing *P. gingivalis* 1435/1449 LPS was very effective at blocking tumor induction. Specifically, while one mouse developed a tumor shortly after controls, one mouse in this group was tumor-free until day 32 and another remained tumor-free at the conclusion of the study (day 50).

Injection of antigen preparations containing *P. gingivalis* 1690 LPS was also somewhat effective at inhibiting tumor induction. While two mice developed tumors shortly after controls, one remained tumor-free until day 34.

Tumor sizes were also reduced in the groups receiving *P. gingivalis* LPS immunomodulator, as shown in FIG. 5A. By day 50, mice injected with antigen and IFA alone, or antigen and *E. coli* LPS, had tumors that were approaching 2000 mm$^3$. In contrast, the mice vaccinated with antigen and *P. gingivalis* 1435/1449 LPS that did develop tumors (two out of three), had mean tumor sizes approximately one-third that of controls. Mice vaccinated with antigen and *P. gingivalis* 1690 LPS had mean tumor sizes of approximately 1200 mm$^3$.

Example 5

*P. gingivalis* Lipid A Functionally Interacts with TLR2 and TLR4

This Example demonstrates that *P. gingivalis* LPS enriched for lipid A species at m/z 1435 and 1449 activates human and mouse TLR2, TLR2 plus TLR1, and TLR4 in transiently transfected HEK 293 cells coexpressing membrane-associated CD14. Cofactor MD-2 was required for functional engagement of TLR4 but not of TLR2 nor TLR2 plus TLR1. In addition, serum-soluble CD14 effectively transferred *P. gingivalis* LPS to TLR2 plus TLR1, but poorly to TLR4. Bone marrow cells obtained from TLR2$^{-/-}$ and TLR4$^{-/-}$ mice also responded to *P. gingivalis* LPS in a manor consistent with the HEK results, demonstrating that *P. gingivalis* LPS can utilize both TLR2 and TLR4. No response was observed from bone marrow cells obtained from TLR2 and TLR4 double-knock-out mice, demonstrating that *P. gingivalis* LPS activation occurred exclusively through either TLR2 or TLR4.

*P. gingivalis*

ATCC 33277 was cultured as described above. LPS was prepared by the cold MgCl$_2$-ethanol procedure above, followed by lipid extraction (Folch et al., supra) and conversion to sodium salts (Peterson et al., *J. Bacteriol.* 165:116-122 (1986)). *E. coli* 0111:B4 LPS (Sigma, St. Louis, Mo.) was subjected to a Folch extraction to remove contaminating phospholipids. All LPS preparations were further treated to remove trace amounts of endotoxin protein as described by Manthey and Vogel, above. A crude LPS extraction procedure also used commercially available TR1 reagent (Yi and Hackett, *Analyst* 125:651-656 (2000)).

Figures 6A, 6B, 6C:
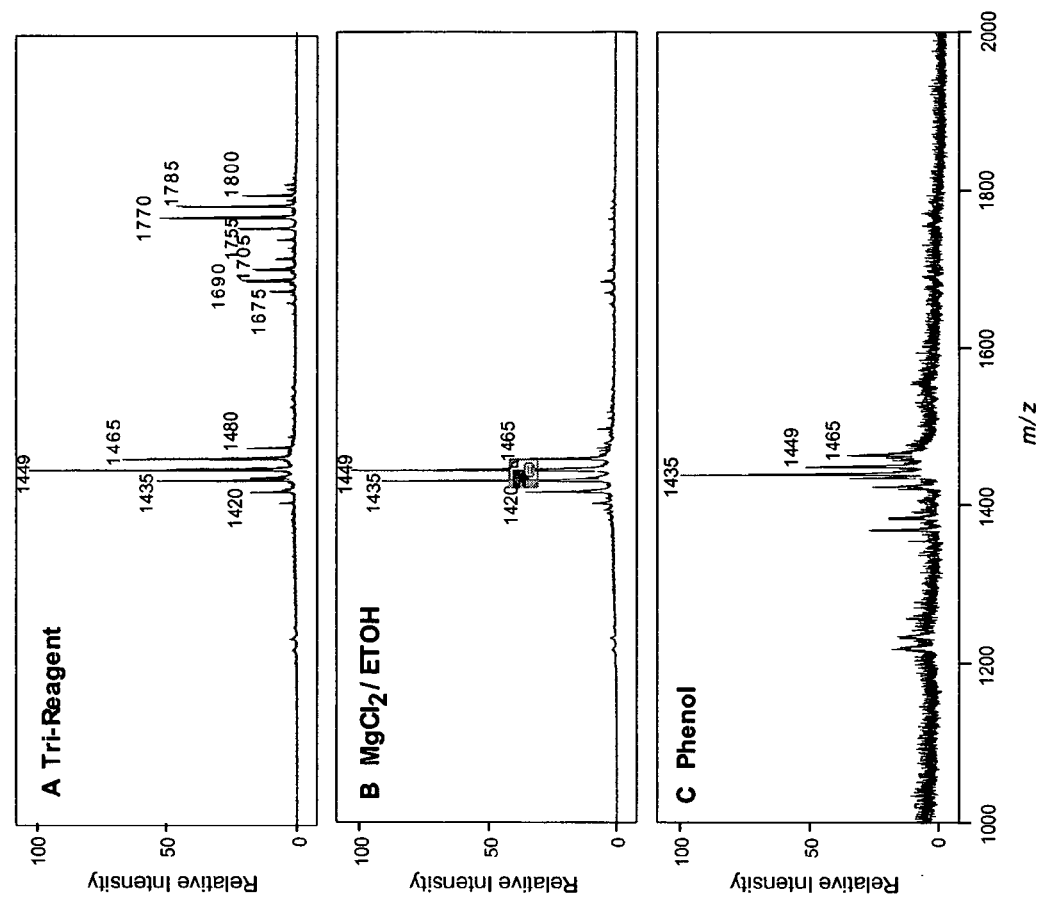
FIGS. 6A-C depict *P. gingivalis* lipid A species by negative ion mass spectrometry, where LPS was obtained by either tri-reagent procedure (FIG. 6A); cold/MgCL$_2$ ETOH procedure (FIG. 6B); or phenol/H$_2$O procedure (FIG. 6C), and lipid A was cleaved and separated from the LPS, and matrix-assisted laser desorption time of flight (MALDI-TOF) was performed. All values given are average mass rounded to the nearest whole number for singly charged deprotonated molecules. Tri-reagent extracted LPS yields two major lipid A mass ions at m/z 1690 and m/z 1770 which are missing or significantly reduced when either MgCl$_2$/ethanol (FIG. 6B) or phenol/water (FIG. 6C) procedures are used to purify the LPS.

TRI reagent extraction of LPS from *P. gingivalis* and subsequent lipid A cleavage revealed numerous major lipid A mass ions that clustered around m/z 1,450, 1,690, and 1,770 (FIG. 6). The lipid A species found around each of these mass ions differed by smaller single methylene units (m/z 1,420 and 1,435 adjacent to 1,449; 1,675 adjacent to 1,690; and 1,705 and 1,755 adjacent to 1,770) and larger single methylene units (m/z 1,465 and 1,480 adjacent to 1,449; 1,705 adjacent to 1,690; and 1,785 and 1,800 adjacent to 1,770). This pattern of different lipid A mass ions is indicative of fatty acid chain length heterogeneity, accounting for some of the different lipid A species. In contrast, LPS extracted from whole cells by the MgCl$_2$-EtOH method was significantly reduced in both clusters of lipid A mass ions centered at m/z 1,690 and m/z 1,770. This preparation, designated Pg LPS$_{1435/1449}$ (see below), revealed major lipid A mass ions at m/z 1,435 and 1,449. In addition, two minor peaks at m/z 1,420 and 1,465 were observed and may be structurally related lipid A mass ions that differ in their fatty acid content. GC/MS of fatty acids present in the Pg LPS$_{1435/1449}$ preparation was performed. There was little or no phospholipid, glycolipid, or lipoprotein contamination in the Pg LPS$_{1435/1449}$ preparation.

The ability of the Pg LPS$_{1435/1449}$ *P. gingivalis* preparation to activate cells through specific TLRs was examined by employing HEK cell transient transfections with different components of the TLR2 and TLR4 activation complexes. An experiment to determine if endogenous receptors on HEK cells were capable of responding to the *P. gingivalis* LPS preparation validated HEK 293 cells as a suitable cell line to examine the interactions of *P. gingivalis* LPS with different exogenously added TLRs. Therefore, experiments described below report the ability of the Pg LPS$_{1435/1449}$ preparation to activate HEK cells above background levels and compare Pg LPS$_{1435/1449}$ activation to that of known TLR ligands.

The abilities of the Pg LPS$_{1435/1449}$ preparation and the synthetic lipopeptide (Pam3CSK4), a known TLR2 agonist, to stimulate HEK 293 cells transiently transfected with human TLR2 (huTLR2) were determined. In these experiments, HEK cells were transfected with human mCD14 with and without MD-2, components of the innate host response known to optimize LPS interactions with TLRs. A shown in FIGS. 7A and 7B, *P. gingivalis* LPS significantly ($P<0.001$; two-sample t test) activated HEK cells through huTLR2 (an eightfold increase at 1 μg of LPS/ml, with or without the addition of MD-2), although it was significantly ($P<0.001$; two-sample test) less active than Pam3CSK4. Additional experiments employing murine TLR2 (muTLR2) with murine MD-2 also demonstrated significant HEK cell activation that was significantly less than that with Pam3CSK4.

Figure 8B:
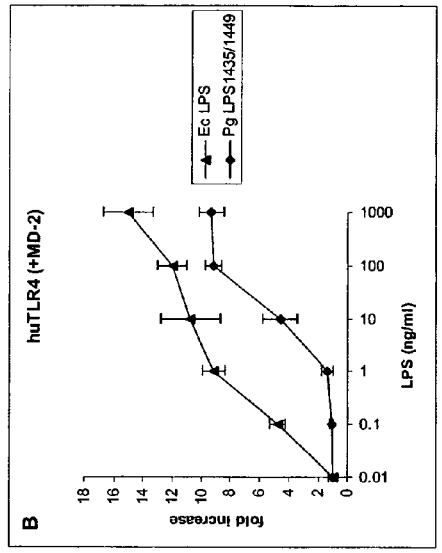
FIG. 8 depicts TLR4 activation with *P. gingivalis* LPS preparations. HEK 293 cells were transiently transfected with mouse mCD14 and muTLR4 (A and C) or human mCD14 and huTLR4 (B and D), with and without mouse and human MD-2, respectively, as indicted in the figure, together with the NF-κB reporter (ELAM-1-firefly luciferase) and the transfection control (β-actin-*Renilla* luciferase). Various doses of *E. coli* and Pg LPS$_{1435/1449}$ were added to the cells for 4 h, the cells were lysed, and the amount of luciferase produced was determined. Values are reported as the fold increase of relative luciferase units (firefly luciferase/*Renilla* luciferase) compared to the nonstimulated control response, which was set at 1. The data presented represent the means and standard deviations from triplicate wells from one experiment and are representative of at least three separate experiments.
Figure 8D:
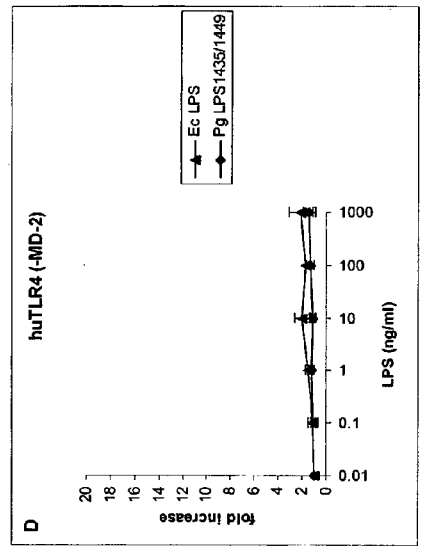
Figure 8A:
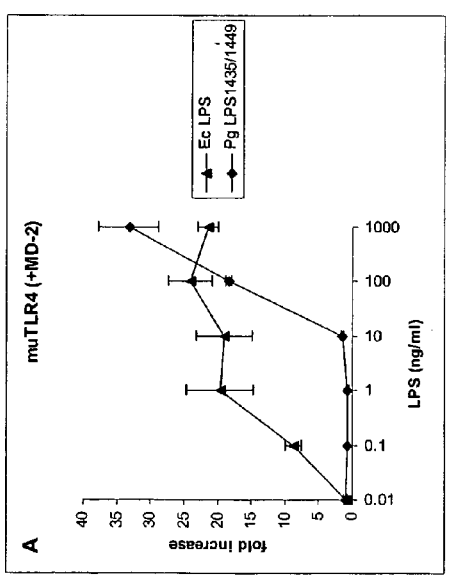
Figure 8C:
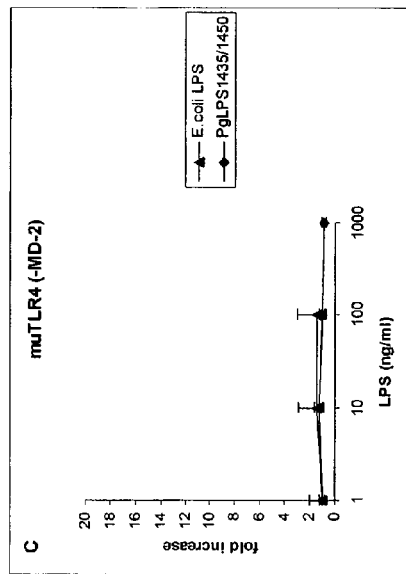

The Pg LPS$_{1435/1449}$ preparation was compared to *E. coli* LPS, a known TLR4 ligand, in its ability to stimulate HEK 293 cells transiently transfected with either muTLR4 or huTLR4. HEK cells transfected with mouse or human mCD14 and either muTLR4 and muMD-2 (FIG. 8A) or huTLR4 and huMD-2 (FIG. 8B) (either all mouse or all human components) displayed significant increases in activation in response to *E. coli* or *P. gingivalis* LPS preparations. However, the *P. gingivalis* LPS preparation required considerably more LPS to achieve significant activation than the *E. coli* LPS. For example, in FIG. 8A, *E. coli* LPS demonstrated significantly greater-than-fivefold HEK cell activation at 0.1 ng/ml. Both mouse and human TLR4-dependent HEK cell activation in response to *E. coli* or *P. gingivalis* LPS was MD-2 dependent (FIGS. 8C and 8D). These data demonstrate that highly purified preparations of *P. gingivalis* LPS are capable of signaling via TLR2, TLR2 plus TLR1, and TLR4.

The ability of *P. gingivalis* LPS to utilize sCD14 for TLR activation was also examined. The role of sCD14 in facilitating LPS activation of TLR-transfected HEK cells was examined by transfecting HEK cells without mCD14 and employing sCD14-depleted human serum as a source for LBP (FIG. 9).

Figure 9A:
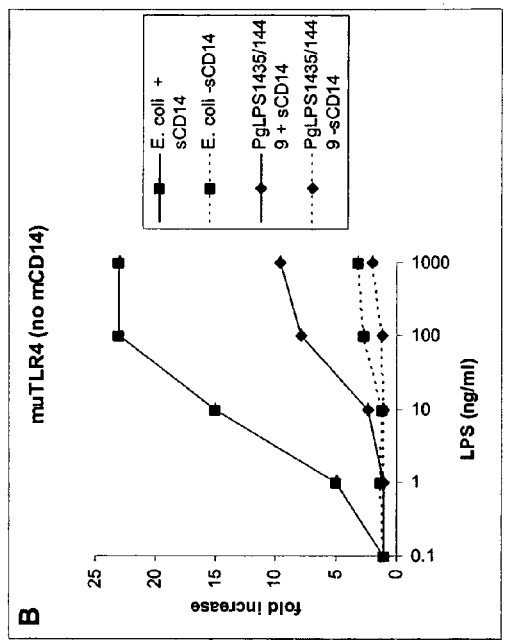
FIG. 9 depicts the contribution of sCD14 for TLR activation by *P. gingivalis* LPS preparations. HEK 293 cells were transiently transfected with MD-2 and with muTLR2 plus TLR1 (A), muTLR4 (B), or huTLR4 (C), together with the NF-κB reporter (ELAM-1-firefly luciferase) and the transfection control (β-actin-*Renilla* luciferase). Various concentrations Pg LPS$_{1435/1449}$ and *E. coli* LPS (B and C) were added to the cells in activation buffer containing either sCD14-depleted human serum as a source for LBP (dotted lines) or FBS as a source for both LBP and sCD14 (solid lines). The HEK cells were incubated with the LPS preparations for 4 h, the cells were lysed, and the amount of luciferase produced was determined. The data presented represent the means and standard deviations from triplicate wells from one experiment and are representative of at least three separate experiments.
Figure 9B:
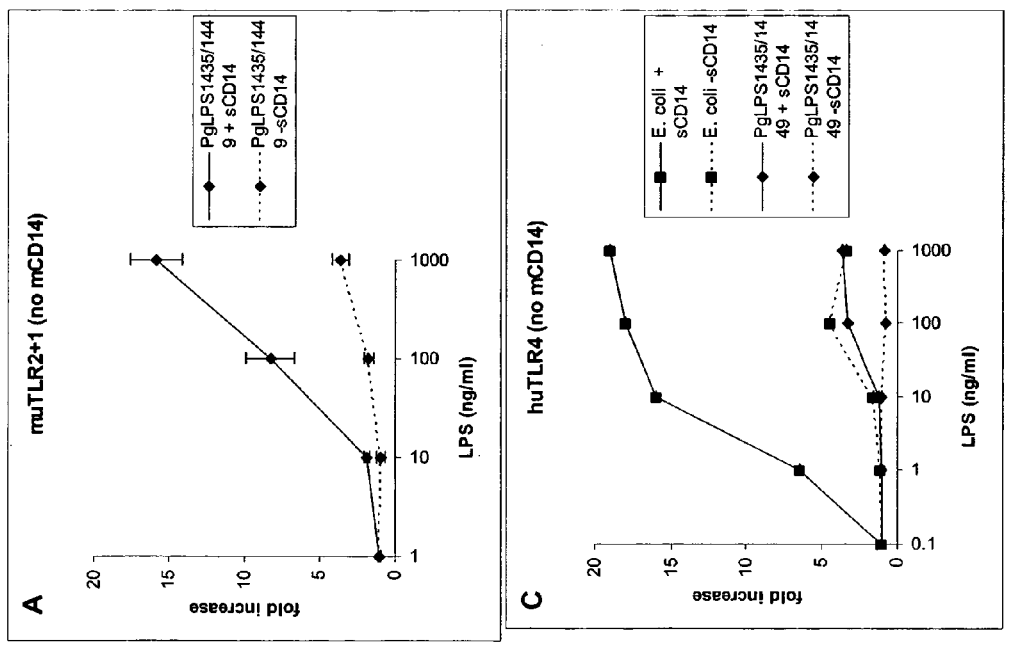
Figure 9C:
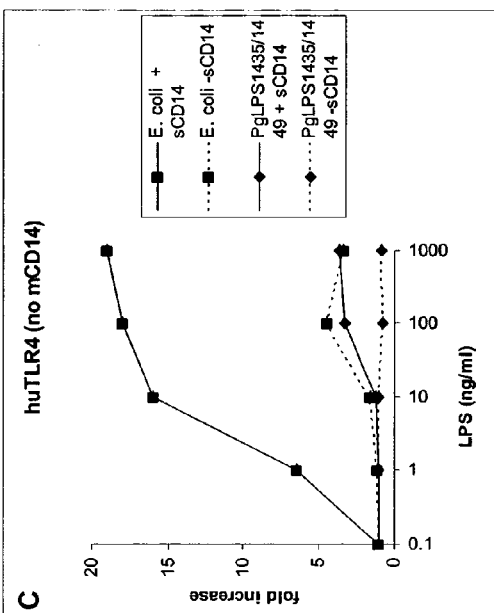
Figure 10A:
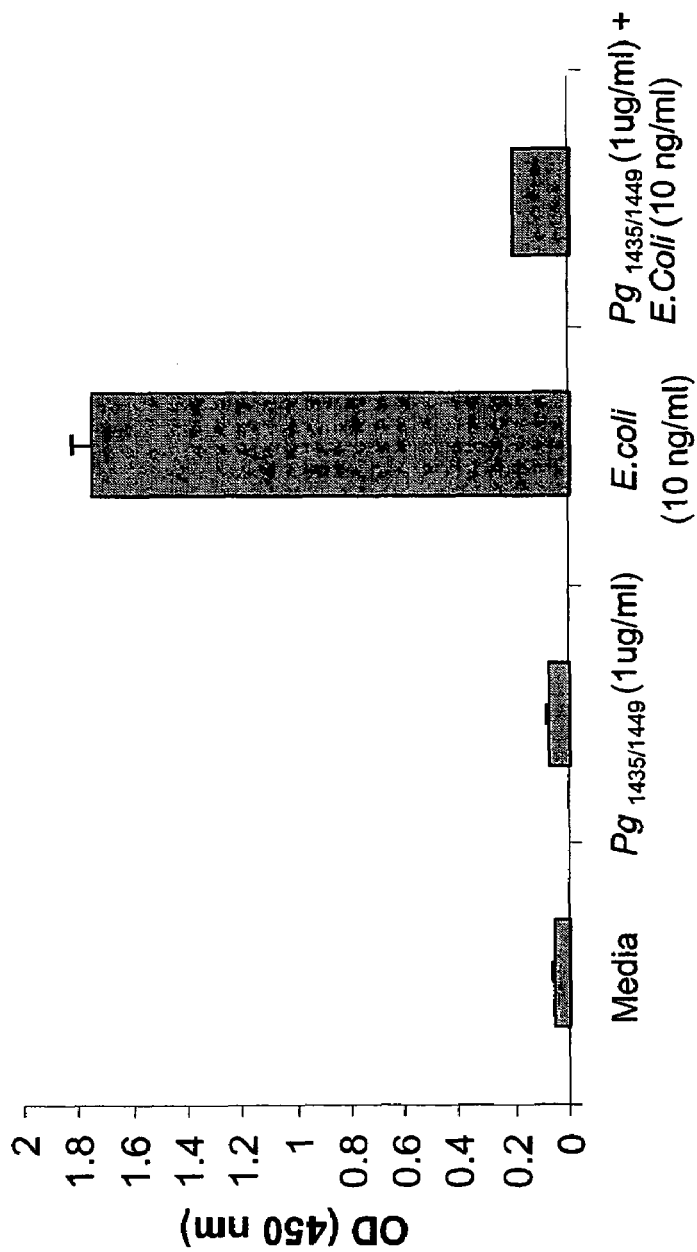

Human serum depleted of sCD14 demonstrated significantly lower muTLR2-plus-TLR1-dependent HEK cell activation for *P. gingivalis* LPS compared to the same transfection that employed FBS during the cell activation (FIG. 9A). In other experiments recombinant sCD14 was added back to the sCD14-depleted serum and HEK cell activation was restored to similar levels as observed when FBS was present in the activation buffer. These experiments demonstrated that sCD14 (human and bovine) can efficiently transfer *P. gingivalis* LPS to muTLR2 plus muTLR1 to facilitate HEK cell activation. Next, the contribution of sCD14 for *P. gingivalis* LPS activation of cells through murine and human TLR4 was examined (FIGS. 9B and C). When FBS was added as a source of both LBP and sCD14, the Pg LPS$_{1435/1449}$ preparation was unable to mediate effective TLR4-dependent HEK cell activation in comparison to that with *E. coli* LPS (FIGS. 9B and C.). This difference in HEK cell activation through TLR4 was most dramatic for huTLR4, where *P. gingivalis* LPS yielded less than fivefold activation, compared to approximately 20-fold for *E. coli* LPS (FIG. 9C). These findings are in contrast to the data obtained with mCD14 (FIG. 8), where maximal TLR4 activation was nearly equivalent for both *E. coli* and *P. gingivalis* LPS. Thus, these data reveal a relatively poor ability of *P. gingivalis* LPS to utilize human sCD14 for huTL The HEK transient-transfection experiments with either TLR2 or TLR4 demonstrated that the Pg LPS$_{1435/1449}$ preparation was able to engage either TLR receptor to activate the NF-κB-dependent reporter construct. The ability of this *P. gingivalis* LPS preparation to activate mouse bone marrow cells obtained from TLR2$^{-/-}$, TLR4$^{-/-}$, and TLR2/4$^{-/-}$ knockout mice was examined to determine if endogenous TLR2 and TLR4 were utilized. Activation was determined by intracellular TNF-α staining and fluorescence-activated cell sorter analysis. Bone marrow cells obtained from either TLR2$^{-/-}$ or TLR4$^{-/-}$ mice responded to the Pg LPS$_{1435/1449}$ preparation, consistent with observations made in HEK cells that demonstrated the *P. gingivalis* LPS preparation could use either TLR2 or TLR4 for host cell activation. Furthermore, cells obtained from TLR2/4 double-knockout mice did not respond to the *P. gingivalis* LPS preparation, demonstrating that the LPS activity observed with this cell type was mediated exclusively through TLR2 and TLR4. In contrast, bone marrow cell responses to *Salmonella minnesota* LPS (a TLR4 ligand) and Pam3CSK4 (a TLR2 ligand) demonstrated that these microbial ligands utilized their respective cognate TLR. These data provide good evidence that *P. gingivalis* LPS can utilize TLR2 and TLR4 under conditions where they are expressed at endogenous levels.

Thus, in this Example, the *P. gingivalis* LPS TLR2 activities observed both in the HEK cell and mouse bone marrow cell systems were attributed to the lipid A mass ions at m/z 1,435 and/or 1,449. The structures for the lipid A mass ions at m/z 1,435 and 1,449 are, tetra-acylated monophosphorylated species (Kumada et al., *J. Bacteriol.* 177:2098-2106 (1995)). The same highly purified *P. gingivalis* LPS preparation was capable of activating HEK and mouse bone marrow cells through TLR4, and both murine and human TLR4/MD-2 systems were capable of responding to *P. gingivalis* LPS. This is unusual since it has been shown that muTLR4 but not huTLR4 can respond to tetra-acylated *E. coli* LPS (Poltorak et al., *Proc. Natl. Acad. Sci. USA,* 97:2163-2167 (2000)). It was also found that MD-2 was not required for *P. gingivalis* LPS TLR2-dependent, or TLR2-plus-TLR1-dependent, HEK cell activation but was necessary for activation with mouse or human TLR4.

Furthermore, sCD14 readily replaced mCD14 to yield highly significant *P. gingivalis* LPS TLR2-plus-TLR1-dependent HEK cell activation, as demonstrated both by significant activation at low LPS concentrations (10 ng/ml) and a greater-than-15-fold increase over background at higher concentrations of LPS. However, huTLR4-dependent HEK cell activation employing sCD14 revealed that the Pg LPS$_{1435/1449}$ preparation only slightly activated these cells above background control levels at 100 and 1,000 ng of LPS/ml. These data demonstrated that the TLR activity of *P. gingivalis* LPS preparations is prone to the presence of accessory molecules, such as soluble or membrane CD14.

The results of HEK cell transfection assays and bone marrow cell activation experiments demonstrate that certain *P. gingivalis* LPS preparations have the ability to interact with either TLR2 or TLR4. Also, the lipid A heterogeneity observed in *P. gingivalis* LPS preparations may reflect an ability of this bacterium to synthesize and express multiple, structurally different forms of lipid A. Alterations in the lipid A structural composition and utilization of multiple TLRs may affect host cell signaling, contributing to the ability of P. gingivalis to remain a persistent colonizer of the oral cavity as well as to induce inflammatory disease.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. An immunomodulator composition for stimulating the immune system of a mammal against an antigen preparation of interest, comprising said antigen preparation of interest, a pharmaceutically acceptable carrier, and an immunomodulator which comprises purified *Porphyromonas gingivalis* lipopolysaccharide (LPS) with a lipid A portion of said LPS having a molecular negative mas ion of 1435 or 1449.

2. The immunomodulator composition of claim 1, wherein the antigen preparation of interest is a tumor antigen.

3. The immunomodulator composition of claim 2, wherein the tumor antigen is Her-2/neu.

4. The immunomodulator composition of claim 2, wherein the tumor antigen is folate receptor, insulin-like growth factor binding protein, carcinoembryonic protein, or CA-125.

5. The immunomodulator composition of claim 1, further comprising an adjuvant.

6. The immunomodulator composition of claim 5, wherein the adjuvant is alum, incomplete Freund's adjuvant, montanide, GM-CSF, imiquimod, resiquimod, or a saponin.

7. The immunomodulator composition of claim 1, wherein the LPS is at least 70% purified.

8. The immunomodulator composition of claim 7, wherein the LPS is at least 90% purified.

9. A method for stimulating a protective immune response against a tumor in a mammal, comprising:
   administering to the mammal a composition which comprises a tumor antigen from said tumor or type of said tumor and an immunomodulator which comprises purified *P. gingivalis* LPS with the lipid A portion of said LPS having a molecular negative mass ion of 1435 or 1449 in an amount sufficient to elicit an immune response which protects against development of said tumor in the mammal.

10. The method according to claim 9, wherein the composition is administered multiple times to said mammal to boost the immune response to said tumor, each administration separated by at least one week.

11. The method according to claim 9, wherein the composition is administered by intramuscular, intravenous, intradermal, subcutaneous, mucosal or intra-tumoral injection.

12. The method according to claim 9, wherein the tumor antigen is Her-2/neu.

13. The method according to claim 9, further comprising an adjuvant.

14. The method according to claim 9, wherein the tumor in the mammal regresses following administration of said composition.

15. The method according to claim 9, wherein the mammal has a risk of developing a tumor but has not yet been diagnosed with a tumor.

16. A method for stimulating an immune response to an antigen of interest in cells obtained from a mammal, comprising:
   contacting the cells in vitro with a composition which comprises the antigen of interest and an immunomodulator which comprises purified *P. gingivalis* LPS having a molecular negative mass ion of 1435 or 1449 in an amount sufficient to elicit an immune response to said antigen of interest.

17. A method for stimulating an immune response against a tumor in a mammal, comprising:
   administering to the mammal a composition which comprises a tumor antigen from said tumor or type of said tumor and an immunomodulator which comprises purified *P. gingivalis* LPS having a molecular negative mass ion of 1690, in an amount sufficient to elicit an immune response against development of said tumor in the mammal.

18. A method for stimulating immune effector cells obtained from a mammal in vitro, comprising:
   administering to said immune effector cells in vitro a composition which comprises an antigen of interest capable of eliciting an in vitro immune response from said immune effector cells to said antigen and an immunomodulator which comprises purified *P. gingivalis* LPS having a molecular negative mass ion of 1690, in an amount sufficient to stimulate said immune effector cells.

19. A method for stimulating an immune response against a tumor in a mammal, comprising:
   administering to the mammal a composition which comprises tumor antigen from said tumor or type of said tumor and an immunomodulator which comprises purified *P. gingivalis* LPS with the lipid A portion of said LPS having a molecular negative mass ion of 1435 or 1449 in an amount sufficient to elicit an immune response against said tumor in the mammal.

20. A method for modulating an immune response against an antigen in a mammal, comprising:
   administering to the mammal a composition which comprises the antigen and an immunomodulator which comprises purified *P. gingivalis* LPS having a molecular negative mass ion of 1435 or 1449 in an amount sufficient to modulate the immune response against the antigen in the mammal.

21. A method for modulating an immune response against an autoimmune disease antigen in a mammal, comprising:
   administering to the mammal a composition which comprises the autoimmune disease antigen and an immunomodulator which comprises purified *P. gingivalis* LPS having a molecular negative mass ion of 1435/1449, in an amount sufficient to modulate the autoimmune disease in the mammal.

22. A method for modulating an immune response against an inflammatory disease antigen in a mammal, comprising:
   administering to the mammal a composition which comprises the inflammatory disease antigen and an immunomodulator which comprises purified *P. gingivalis* LPS having a molecular negative mass ion of 1435/1449, in an amount sufficient to modulate the inflammatory disease in the mammal.

23. A method for modulating an immune response against a graft-versus-host disease antigen in a mammal, comprising:
   administering to the mammal a composition which comprises the graft-versus-host disease antigen and an immunomodulator which comprises purified *P. gingivalis* LPS having a molecular negative mass ion of 1435/1449, in an amount sufficient to modulate the graft-versus-host disease in the mammal.

* * * * *